US009187787B2

(12) United States Patent
Rotem

(10) Patent No.: US 9,187,787 B2

(45) Date of Patent: Nov. 17, 2015

(54) METHOD OF DIAGNOSING AND TREATING CANCER

(75) Inventor: Karni Rotem, Mevasseret Zion (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/704,701

(22) PCT Filed: Jun. 16, 2011

(86) PCT No.: PCT/IL2011/000484

§ 371 (c)(1), (2), (4) Date: Dec. 17, 2012

(87) PCT Pub. No.: WO2011/158243

PCT Pub. Date: Dec. 22, 2011

(65) Prior Publication Data

US 2013/0089563 A1 Apr. 11, 2013

(51) Int. Cl.

*C12N 15/11* (2006.01)
*C12Q 1/68* (2006.01)

(52) U.S. Cl.

CPC ........ *C12Q 1/6886* (2013.01); *C12Q 2600/112* (2013.01); *C12Q 2600/118* (2013.01); *C12Q 2600/136* (2013.01); *C12Q 2600/158* (2013.01)

(58) Field of Classification Search

None
See application file for complete search history.

(56) References Cited

U.S. PATENT DOCUMENTS

| | | | | |
|---|---|---|---|---|
| 6,251,586 | B1 | 6/2001 | Mulshine et al. | |
| 6,500,625 | B1 | 12/2002 | Mulshine et al. | |
| 2003/0036068 | A1 | 2/2003 | Kopreski | |
| 2005/0153918 | A1* | 7/2005 | Chabot et al. | 514/44 |
| 2007/0212738 | A1 | 9/2007 | Haley et al. | |

FOREIGN PATENT DOCUMENTS

| | | |
|---|---|---|
| WO | WO 03/102185 | 12/2003 |
| WO | WO 2011/158243 | 12/2011 |

OTHER PUBLICATIONS

Zhou et al, Breast Can Res and Treat, 66:217-224, 2001.*
Communication Relating to the Results of the Partial International Search Dated Sep. 9, 2011 From the International Searching Authority Re. Application No. PCT/IL2011/000484.
International Search Report and the Written Opinion Dated Dec. 14, 2011 From the International Searching Authority Re. Application No. PCT/IL2011/000484.
Goldenberg "Trastuzumab, A Recombinant DNA-Derived Humanized Monoclonal Antibody, A Novel Agent for the Treatment of Metastatic Breast Cancer", Clinical Therapeutics, XP000918210, 21(2): 309-318, Jan. 1, 1999. Abstract.
Iiamrita et al. "Identification of Tumor Antigens That Elicit a Humoral Immune Response in Breast Cancer Patients' Sera by Serological Proteome Analysis (SERPA)", Clinical Chimica Acta, XP022699940, 393(2): 95-102, Jul. 17, 2008. Fig.2.
Leygue et al. "Mammaglobin, A Potential Marker of Breast Cancer Nodal Metastasis", Journal of Pathology, XP003025610, 189(1): 28-33, Sep. 1, 1999. Abstract, Fig.2.
Sueoka et al. "Detection of Plasma HnPNP B1 mRNA, A New Cancer Biomarker, in Lung Cancer Patients by Quantitative Real-Time Polymerase Chain Reaction", Lung Cancer, XP025286980, 48(1): 77-83, Apr. 1, 2005. Abstract.
Zhou et al. "A Marker for Early lung Cancer, Heterogeneous Nuclear Ribonucleoprotein-A2/B1 (HnRNP-A2/B1) Is Frequently Expressed in Breast Carcinogenetics", Proceedings of the Annual Meeting of the American Association for Cancer Research, XP008142299, 38: 209, #1407, Apr. 16, 1997. Abstract.
Zhou et al. "Differential Expression of the Early Lung Cancer Detection Marker, Heterogeneous Nuclear Ribonucleoprotein-A2/B1 (HnRNP-A2/B1) in Normal Breast and Neoplastic Breast Cancer", Breast Cancer Research and Treatment, XP55005989, 66(3): 217-224, Apr. 1, 2001. Abstract.
Communication Pursuant to Article 94(3) EPC Dated Oct. 1, 2013 From the European Patent Office Re. Application No. 11731512.7.
International Preliminary Report on Patentability Dated Jan. 3, 2013 From the International Bureau of WIPO Re. Application No. PCT/IL2011/000484.

* cited by examiner

*Primary Examiner* — Tracy Vivlemore
*Assistant Examiner* — Kate Poliakova

(57) ABSTRACT

A method of diagnosing and treating a glioma or a breast cancer is disclosed. The method of diagnosing comprises analyzing an amount or activity of heterogeneous nuclear ribonucleoprotein A2/B1 (hnRNP A2/B1) in a brain or breast cell sample of the subject, wherein an up-regulation in an amount or activity of hnRNP A2/B1 beyond a predetermined threshold with respect to a control cell sample is indicative of the breast cancer or glioma. The method may also be used for staging the cancer and for predicting patient's prognosis of survival. The method of treating glioblastoma and metastatic breast cancer includes inhibiting the expression and/or activity of hnRNP A2/B1.

4 Claims, 23 Drawing Sheets
(15 of 23 Drawing Sheet(s) Filed in Color)

Gene expression
Probability of survival
Probability of Survival
Days in Study
Days in study Gene copy number
Probability of survival
Days in Study
Days in study

FIG. 4A

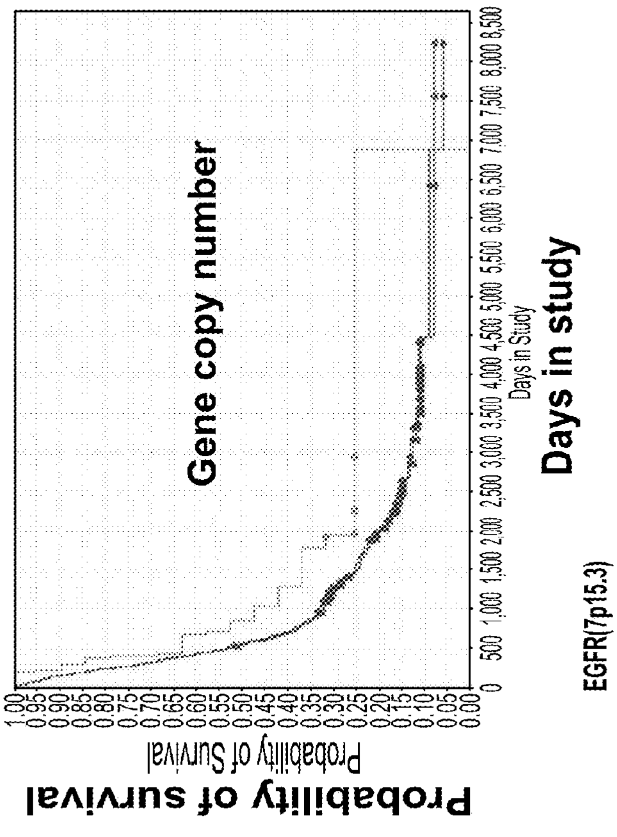

EGFR(7p15.3)
Number of samples in group:
Amplified: 325 Deleted: 19
Log-rank p-value(for significance of difference of survival between group of samples)
Amplified vs. Deleted: 0.2160

FIG. 4B

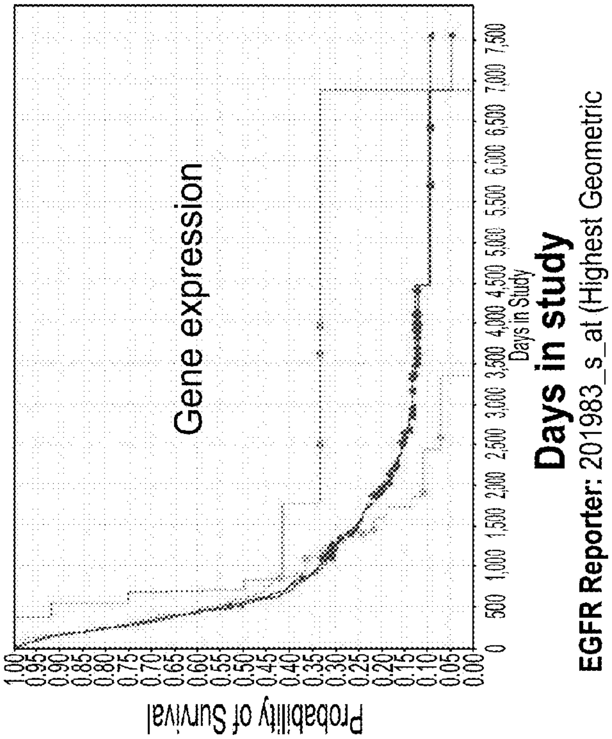

EGFR Reporter: 201983_s_at (Highest Geometric Mean Intensity) Number of samples in group: Up-Regulated: 275 Down-Regulated: 12 Intermediate: 57 Log-rank p-value(for significance of difference of survival between group of samples) Up-Regulated vs. Intermediate: 0.6632475584 Up-Regulated vs. Down-Regulated: 0.0924022265 Down-Regulated vs. Intermediate: 0.0386996729 Up-Regulated vs. all other samples: 0.6605643372 Down-Regulated vs. all other samples: 0.0784758815 Intermediate vs. all other samples: 0.5501380879

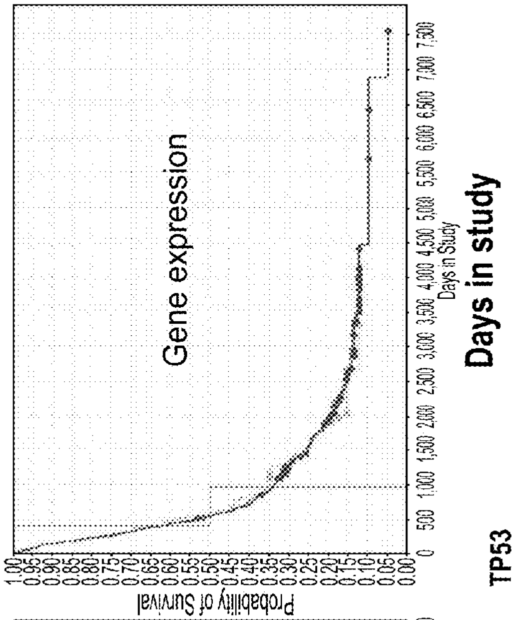

TP53
Number of samples in group:
Up-Regulated: 276 Down-Regulated: 2
Intermediate: 66
Log-rank p-value(for significance of difference of survival between group of samples) Up-Regulated vs. Intermediate: 0.8996174675 Up-Regulated vs. Down-Regulated: 0.7240315141 Down-Regulated vs. Intermediate: 0.6622801978
Up-Regulated vs. all other samples: 0.9428911468 Down-Regulated vs. all other samples: 0.7103846237
Intermediate vs. all other samples: 0.8879333432

FIG. 5D

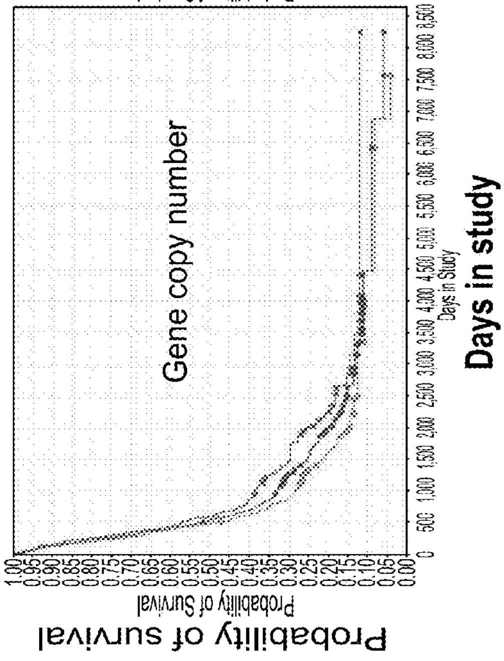

TP53(17p13.1)
Number of samples in group:
Amplified: 158 Deleted: 186
Log-rank p-value(for significance of difference of survival between group of samples) Amplified vs. Deleted: 0.0648616343

FIG. 5C

HNRNPA1
Number of samples in group:
Up-Regulated: 2
Intermediate: 342
Log-rank p-value(for significance of difference of survival between group of samples) Up-Regulated vs. Intermediate: 0.9660533414

HNRNPA1(12p13.33)
Number of samples in group:
Amplified: 321
Deleted: 23
Log-rank p-value(for significance of difference of survival between group of samples)
Amplified vs. Deleted: 0.4227139388

SFRS1

Number of samples in group:

Up-Regulated: 72 Intermediate: 271

Log-rank p-value(for significance of difference of survival between group of samples) Up-Regulated vs. Intermediate: 0.1474297111

FIG. 8A
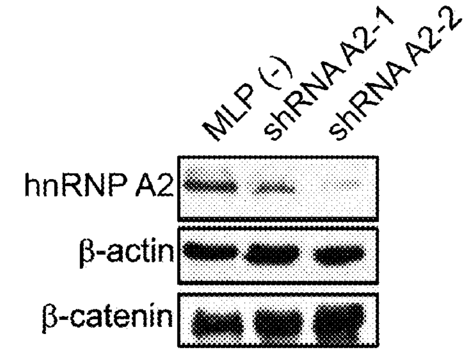
FIG. 8B
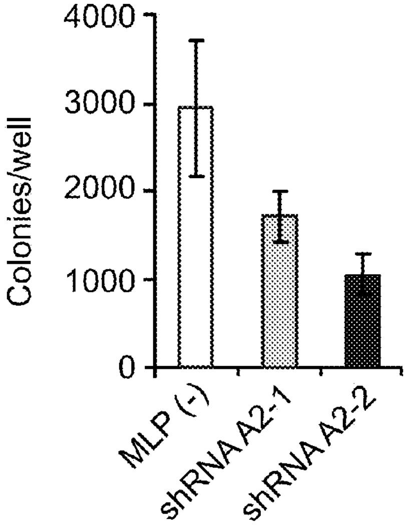
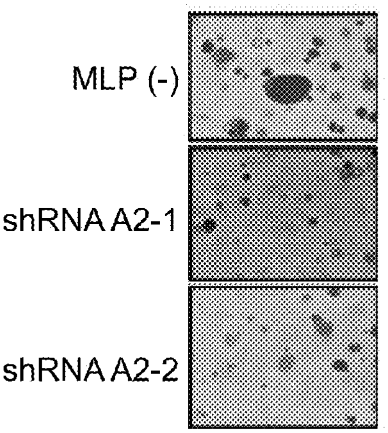
FIG. 8C
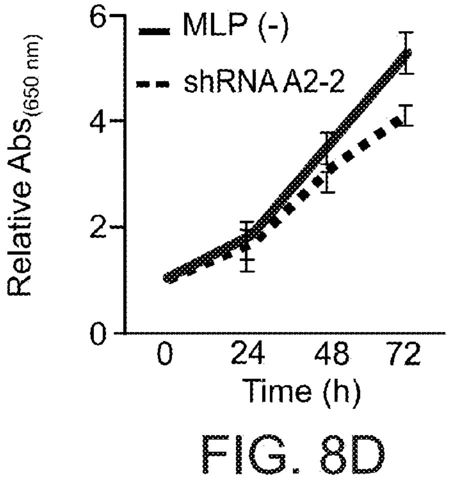
FIG. 8D

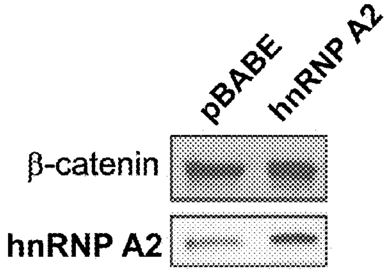
FIG. 11A
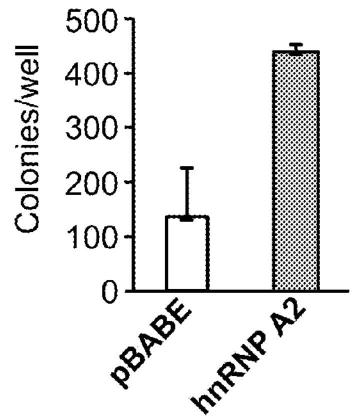
FIG. 11B
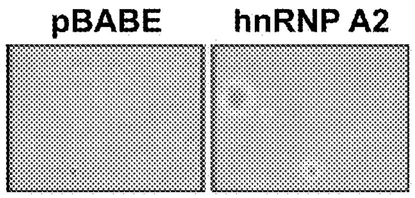
FIG. 11C
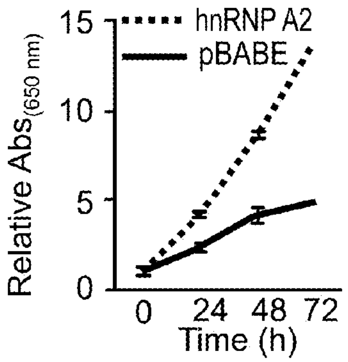
FIG. 11D
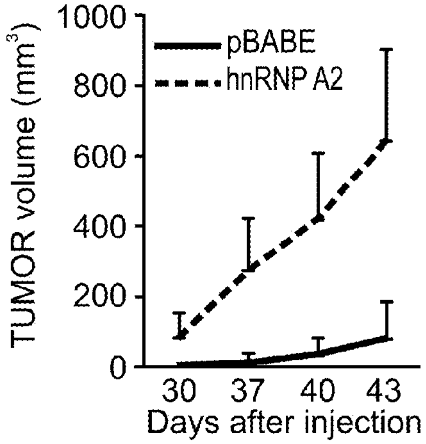
FIG. 11E
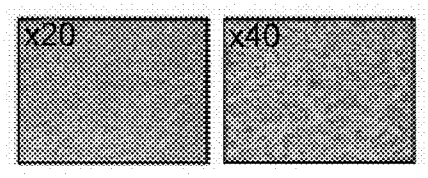
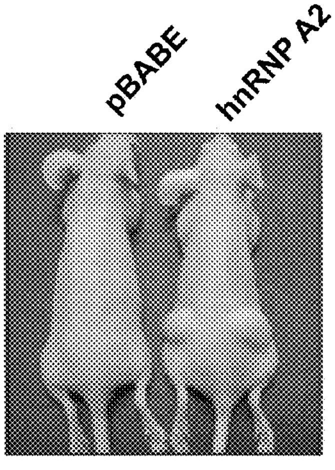
FIG. 11G
FIG. 11F

METHOD OF DIAGNOSING AND TREATING CANCER

RELATED APPLICATIONS

This application is a National Phase of PCT Patent Application No. PCT/IL2011/000484 having International filing date of Jun. 16, 2011, which claims the benefit of priority under 35 USC §119(e) of U.S. Provisional Patent Application No. 61/355,170 filed on Jun. 16, 2010. The contents of the above applications are all incorporated by reference as if fully set forth herein in their entirety.

FIELD AND BACKGROUND OF THE INVENTION

The present invention, in some embodiments thereof, relates to methods of diagnosing and treating cancer and, more specifically breast cancer and brain cancer.

The process of alternative splicing is widely misregulated in cancer and many tumors express new splicing isoforms which are absent in the corresponding normal tissue. Many oncogenes and tumor suppressors are differentially spliced in cancer cells and it has been shown that many of these cancer-specific isoforms contribute to the transformed phenotype of cancer cells. However, the contribution of alternative splicing regulators to cancer development has been largely unknown. Only recently the first functional evidence showed that some splicing factors can act as potent oncogenes and are up-regulated in human cancers. hnRNP proteins are abundant RNA-binding proteins expressed in most human tissues. The hnRNP A/B family is a subset of hnRNP proteins with closely related sequences and a conserved modular structure. They can affect alternative splicing, frequently by antagonizing SR proteins, in part through the recognition of exonic splicing silencers (ESS) elements. Additional functions of these proteins in post-splicing events, such as mRNA trafficking, and replication and transcription of cytoplasmic RNA viruses, have also been reported. Recent studies have shown that hnRNP A1 also affects the maturation of specific miRNAs among them pre-miR-18a which is part of a cluster of miRNAs with oncogenic activity (oncomirs). Previous studies showed overexpression of hnRNP A1 and hnRNP A2/B1 in lung and breast cancer (Fielding P et al., *Clin Cancer Res* 1999; 5: 4048-52, Zhou J et al., *Lung Cancer* 2001; 34: 341-50). Moreover, knockdown of hnRNP A1 and A2/B1 in breast cancer cells induced apoptosis which was specific for cancer cells (Patry C et al., *Cancer Res* 2003; 63: 7679-88).

U.S. Patent Application Publication No. 2007/0212738 teaches method of assessing responsiveness of a cancer patient to an EGFR kinase inhibitor, wherein high expression levels of heterogeneous nuclear ribonucleoprotein A2/B1 correlate with a tumor that will respond less effectively to treatment with an EGFR kinase inhibitor.

U.S. Pat. No. 6,251,586 teaches methods of early diagnosis of breast cancer by analyzing expression levels of heterogeneous nuclear ribonucleoprotein A2/B1. In addition, U.S. Pat. No. 6,251,586 teaches methods of treating cancer by administering antisense oligonucleotides which are substantially complementary to heterogeneous nuclear ribonucleoprotein A2/B1.

SUMMARY OF THE INVENTION

According to an aspect of some embodiments of the present invention there is provided a method of staging a breast cancer in a subject in need thereof, the method comprising analyzing an amount or activity of heterogeneous nuclear ribonucleoprotein A2/B1 (hnRNP A2/B1) in a breast cell sample of the subject, wherein an up-regulation in an amount or activity of hnRNP A2/B1 beyond a predetermined threshold with respect to a control breast cell sample is indicative of a stage of breast cancer.

According to an aspect of some embodiments of the present invention there is provided a method of diagnosing a glioma in a subject in need thereof, the method comprising analyzing an amount or activity of heterogeneous nuclear ribonucleoprotein A2/B1 (hnRNP A2/B1) in a brain cell sample of the subject, wherein an up-regulation in an amount or activity of hnRNP A2/B1 beyond a predetermined threshold with respect to a control brain cell sample is indicative of the glioma.

According to an aspect of some embodiments of the present invention there is provided a method of staging a glioma in a subject in need thereof, the method comprising analyzing an amount or activity of heterogeneous nuclear ribonucleoprotein A2/B1 (hnRNP A2/B1) in a brain cell sample of the subject, wherein an up-regulation in an amount or activity of hnRNP A2/B1 beyond a predetermined threshold with respect to a control brain cell sample is indicative of stage of glioma.

According to an aspect of some embodiments of the present invention there is provided a method of treating a glioma in a subject in need thereof, the method comprising administering to the subject a therapeutically effective amount of an agent which down-regulates an amount or activity of hnRNP A2/B1 or a target thereof, thereby treating the glioma.

According to an aspect of some embodiments of the present invention there is provided a method of treating a metastasized breast cancer in a subject in need thereof, the method comprising administering to the subject a therapeutically effective amount of an agent which down-regulates an amount or activity of hnRNP A2/B1 or a target thereof, thereby treating the metastasized breast cancer.

According to an aspect of some embodiments of the present invention there is provided a method of selecting an agent useful for the treatment of metastatic breast cancer or a glioma comprising:

(a) contacting the agent with a population of cells; and (b) analyzing an expression of a marker selected from the group consisting of hnRNP A2/B1, RON and hnRNP A1, wherein a decrease in expression of the marker is indicative of an agent useful for treating the metastatic breast cancer or glioma.

According to some embodiments of the invention, the glioma is selected from the group consisting of anaplastic astrocytoma, glioblastoma multiforme and oligodendroglioma.

According to some embodiments of the invention, the analyzing is effected at the RNA level or the protein level.

According to some embodiments of the invention, the analyzing an activity of hnRNP A2/B1 is effected by analyzing for a presence of exon 7B of hnRNPA1.

According to some embodiments of the invention, the method further comprises informing the subject of the results of the analyzing.

According to some embodiments of the invention, the method further comprises treating the subject based on the results of the analyzing.

According to some embodiments of the invention, the agent is a polynucleotide agent.

According to some embodiments of the invention, the agent is an antibody.

According to some embodiments of the invention, the polynucleotide agent is an siRNA.

According to some embodiments of the invention, the agent is a small molecule.

According to some embodiments of the invention, the target is RON.

According to some embodiments of the invention, the target is hnRNP A1.

According to some embodiments of the invention, the method further comprises synthesizing a pharmaceutical composition comprising the agent which is indicative for treating the metastatic breast cancer or glioma.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
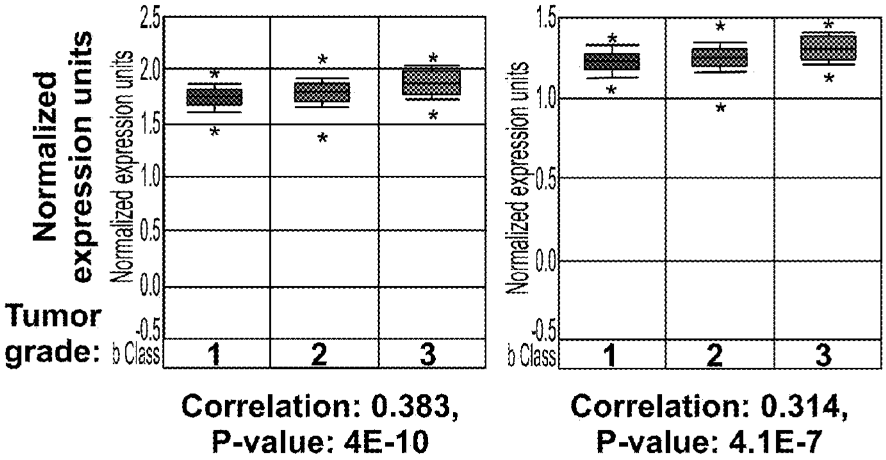
Figure 1B:
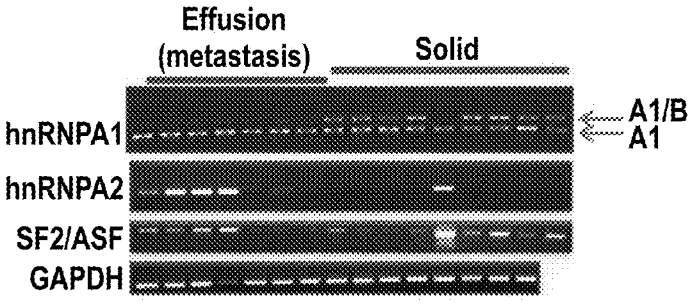
Figure 1C:
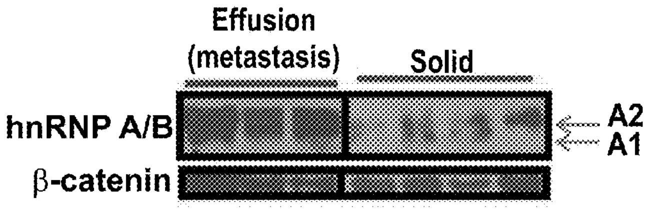

FIGS. 1A-C are graphs and photographs illustrating that hnRNP A2/B1 expression correlates with breast cancer tumor grade and that hnRNP A2/B1 is overexpressed in metastatic effusions but not in primary breast tumors.

FIG. 1A. hnRNP A2/B1 expression in different grades of breast tumor in two different microarray analysis experiments. Data taken from the Oncomine database.

FIG. 1B. hnRNP A1 and A2 expression in breast tumor samples from primary solid tumors and metastatic effusion state analyzed by RT-PCR.

FIG. 1C. hnRNP A/B proteins expression in primary solid tumors and metastatic effusion samples was analyzed by Western blotting using anti pan-hnRNP A/B proteins antibody.

Figure 2A:
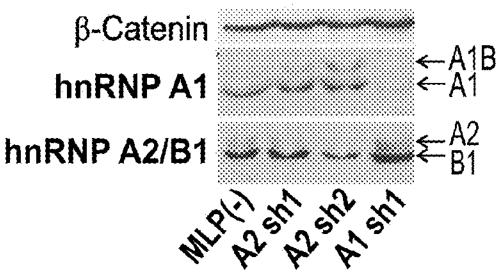
Figure 2B:
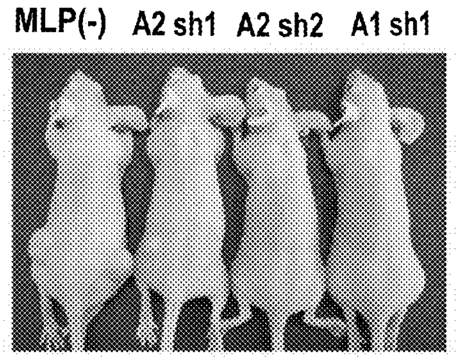
Figure 2C:
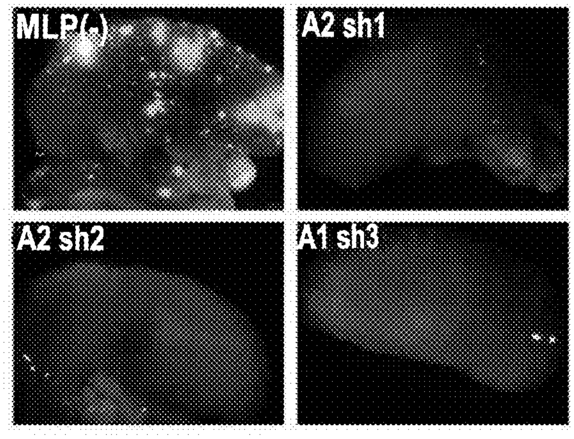

FIGS. 2A-C are photographs illustrating that knockdown of hnRNP A2/B1 and A1 inhibits tumorigenesis and metastasis of the metastatic breast cancer cell line MDA-MB-231.

FIG. 2A. MDA-MB-231 cells were transduced with the indicated retroviruses and after selection were analyzed by Western blotting using the indicated antibodies. Isoforms A1B of hnRNP A1 and B1 of hnRNP A2/B1 are indicated by arrows.

FIG. 2B. Cells described in FIG. 2A were injected (8 injection per construct) ($3\times10^6$ cells/injection site) into the rare flanks of atimic nude mice in matrigel suspension, and tumor volume was measured bi-weekly. Pictures were taken two months after injection.

FIG. 2C. Two months after injection mice were sacrificed and lungs were visualized under fluorescent dissecting scope. Green foci are metastasis of the GFP-labeled MDA-MB-231 cells.

FIGS. 3A-D illustrate that hnRNP A2/B1 is up-regulated in brain tumors and the expression and gene copy number of HNRPA2/B1 are inversely correlated with glioma patient survival.

(A). hnRNP A2/B1 expression in samples of glioblastoma, oligodendrogioma and astrocytoma patient (red) compared to normal brain samples (blue). Data taken from Oncomine (wwwdotworldwidewebdotoncominedotorg).

(B). Q-RT-PCR quantitation of hnRNP A2 expression was performed on total RNA extracted from normal brain (Blue) and glioblastoma WHO grade IV tumors (Gray and Red) columns. Red columns represent tumor samples in which hnRNP A2 expression is more than two-fold over the average expression of the normal brain samples (normalized as 1 and represented as black line).

(C). Kaplan-Meier survival plots show the survival of glioma patients with differential expression of hnRNP A2/B1: Samples with up-regulation (red line) n=28. Samples with intermediate expression (yellow) n=316. The blue line represents the survival of all glioma patients. Log-rank p-value (Up-regulated vs Intermediate): 7.89948E-5. Data based on the National Cancer Institute REMBRANDT data set (wwwdotrembrandtdotmcidotnih/gov).

(D). Kaplan-Meier plots show the correlation between HNRPA2B1 gene copy number and glioma patient survival. Samples with gene amplification (red line) n=172. Samples with gene deletion (green line) n=179. Blue line represents the survival of all glioma patients. Log-rank p-value (Up-regulated vs Intermediate): 1.54771E-5. Data based on the National Cancer Institute REMBRANDT data set (wwwdotrembrandtdotmcidotnih/gov).

FIGS. 4A-D are Kaplan-Meier plots illustrating that the expression and gene copy number of EGFR and MYC do not correlate with glioma patient survival.

(FIG. 4A). Kaplan-Meier plots show the correlation between EGFR gene copy number and glioma patient survival. Samples with gene amplification (red line) n=325. Samples with gene deletion (green line) n=19. Blue line represents the survival of all glioma patients. Log-rank p-value (Amplified vs. deleted): 0.216. Data based on the National Cancer Institute REMBRANDT data set (wwwdotrembrandtdotmcidotnih/gov).

(FIG. 4B). Kaplan-Meier survival plots show the survival of glioma patients with differential expression of EGFR: Samples with up-regulation (red line) Down-regulation (green line) Samples with intermediate expression (yellow). The blue line represents the survival of all glioma patients. Number of samples in group: Up-Regulated: 275 Down-Regulated: 12 Intermediate: 57 Log-rank p value (for significance of difference of survival between group of samples) Up-Regulated vs. Intermediate: 0.663 Up-Regulated vs. Down-Regulated: 0.092 Down-Regulated vs. Intermediate: 0.038 Up-Regulated vs. all other samples: 0.660 Down-Regulated vs. all other samples: 0.078 Intermediate vs. all other samples: 0.550 Data based on the National Cancer Institute REMBRANDT data set (wwwdotrembrandtdotmcidotnih/gov).

Figures 4C, 4D:
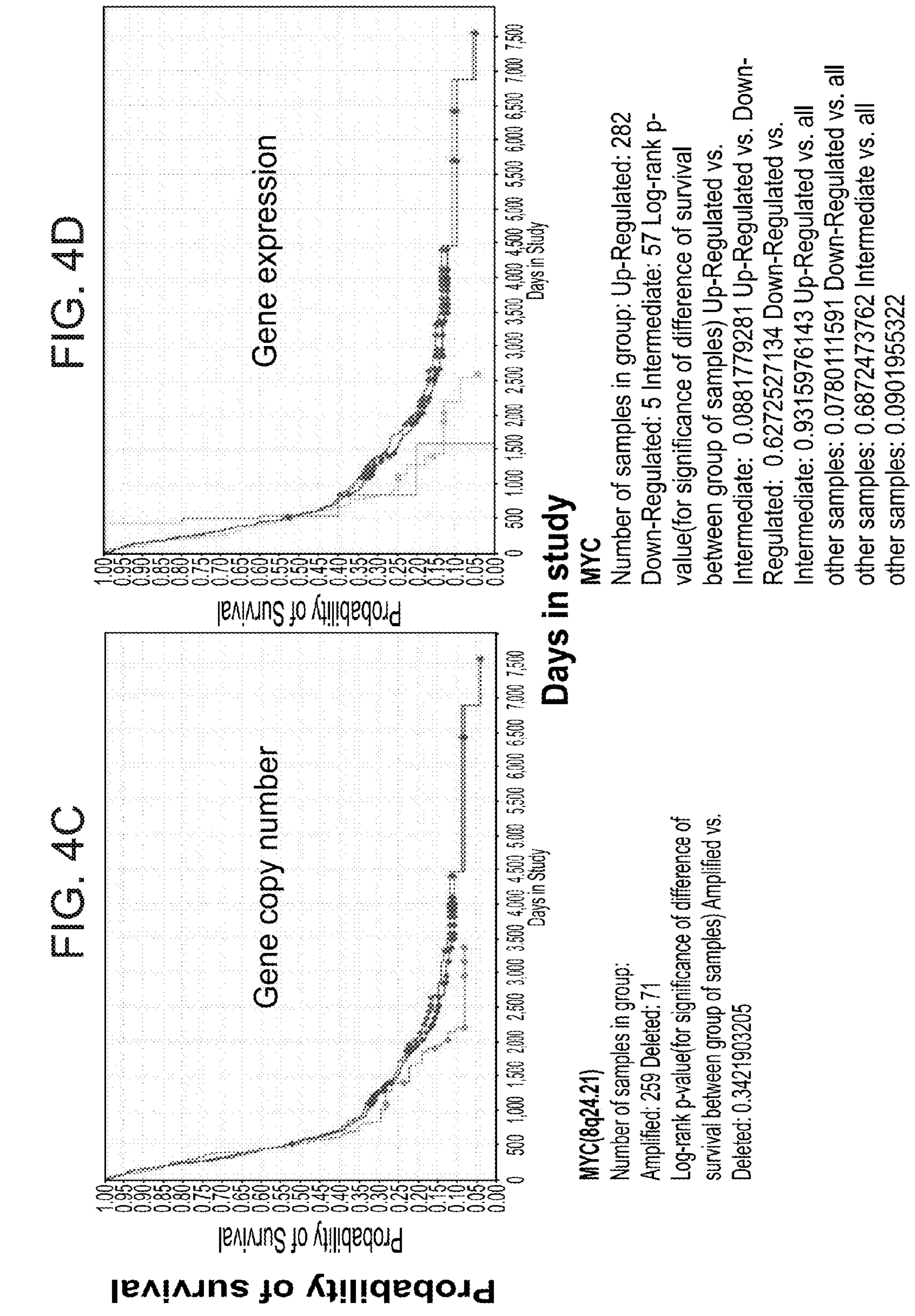

(FIG. 4C). Kaplan-Meier plots show the correlation between MYC gene copy number and glioma patient survival. Samples with gene amplification (red line) n=259. Samples with gene deletion (green line) n=71. Blue line represents the survival of all glioma patients. Log-rank p-value (Amplified vs deleted): 0.342. Data based on the National Cancer Institute REMBRANDT data set (wwwdotrembrandtdotmcidotnih/gov).

(FIG. 4D). Kaplan-Meier survival plots show the survival of glioma patients with differential expression of MYC: Samples with up-regulation (red line) Down-regulation (green line) Samples with intermediate expression (yellow). The blue line represents survival of all glioma patients. Number of samples in group: Up-Regulated: 282 Down-Regulated: 5 Intermediate: 57 Log-rank p-value (for significance of difference of survival between group of samples) Up-Regulated vs. Intermediate: 0.088 Up-Regulated vs. Down-Regulated: 0.627 Down-Regulated vs. Intermediate: 0.931 Up-Regulated vs. all other samples: 0.078 Down-Regulated vs. all other samples: 0.687 Intermediate vs. all other samples: 0.090. Data based on the National Cancer Institute REMBRANDT data set (wwwdotrembrandtdotmcidotnih/gov).

FIGS. 5A-D are Kaplan-Meier plots illustrating that expression and gene copy number of TP73 and TP53 do not correlate with glioma patient survival.

Figure 5A:
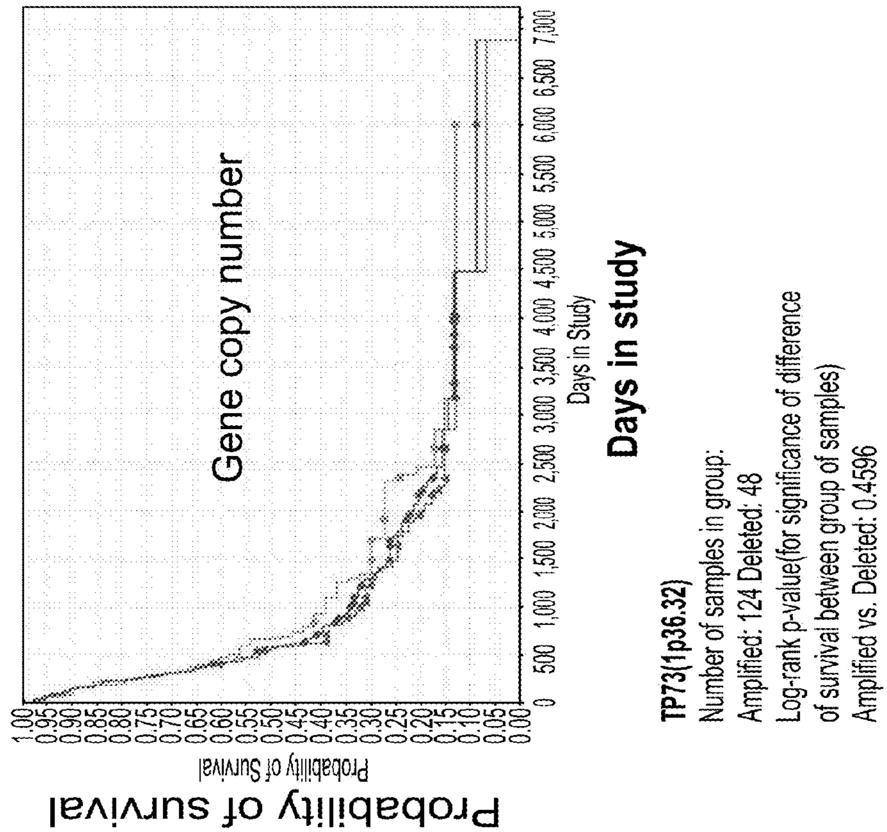

(FIG. 5A). Kaplan-Meier plots show the correlation between TP73 gene copy number and glioma patient survival. Samples with gene amplification (red line) n=124. Samples with gene deletion (green line) n=48. Blue line represents the survival of all glioma patients. Log-rank p-value (Amplified vs. Deleted): 0.459. Data based on the National Cancer Institute REMBRANDT data set.

Figure 5B:
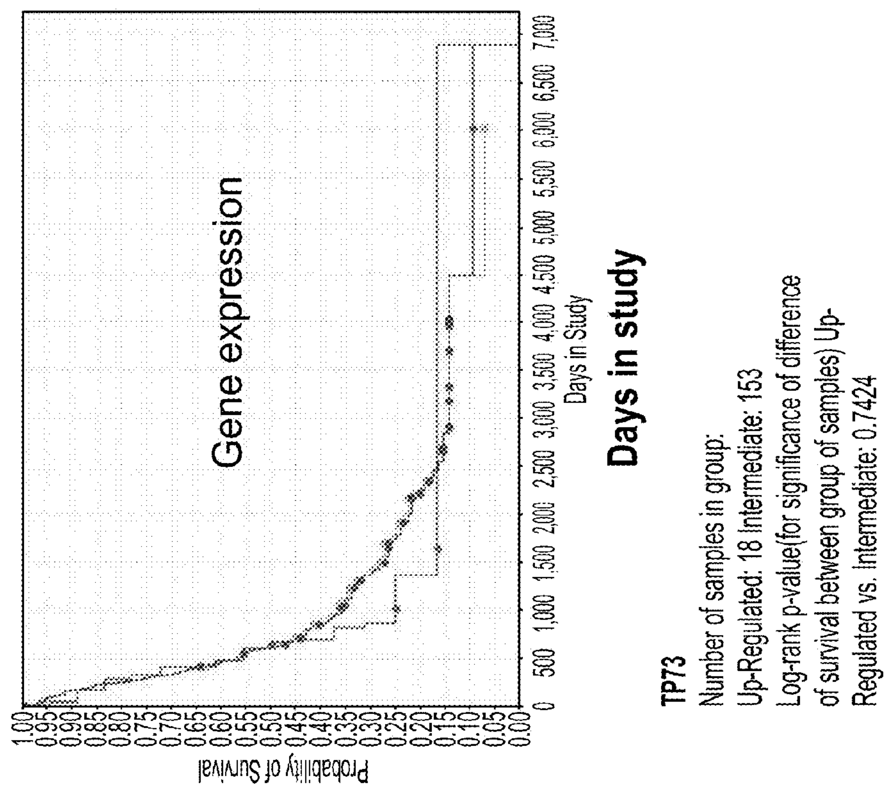

(FIG. 5B). Kaplan-Meier survival plots show the survival of glioma patients with differential expression of TP73: Samples with up-regulation (red line) Down-regulation (green line) Samples with intermediate expression (yellow). The blue line represents the survival of all glioma patients. Number of samples in group: Up-Regulated: 18. Intermediate: 153 Log-rank p-value (for significance of difference of survival between group of samples) Up-Regulated vs. Intermediate: 0.742. Data based on the National Cancer Institute REMBRANDT data set.

(FIG. 5C). Kaplan-Meier plots show the correlation between TP53 gene copy number and glioma patient survival. Samples with gene amplification (red line) n=158. Samples with gene deletion (green line) n=186. Blue line represents the survival of all glioma patients. Log-rank p-value (Amplified vs deleted): 0.064. Data based on the National Cancer Institute REMBRANDT data set.

(FIG. 5D). Kaplan-Meier survival plots show the survival of glioma patients with differential expression of TP53: Samples with up-regulation (red line) Down-regulation (green line) Samples with intermediate expression (yellow). The blue line represents survival of all glioma patients. Number of samples in group: Up-Regulated: 276 Down-Regulated: 2 Intermediate: 66 Log-rank p-value (for significance of difference of survival between group of samples) Up-Regulated vs. Intermediate: 0.899 Up-Regulated vs. Down-Regulated: 0.724. Down-Regulated vs. Intermediate: 0.662 Up-Regulated vs. all other samples: 0.942 Down-Regulated vs. all other samples: 0.710 Intermediate vs. all other samples: 0.887. Data based on the National Cancer Institute REMBRANDT data set.

FIGS. 6A-D are Kaplan-Meier plots illustrating that the expression and gene copy number of PTEN correlates and AKT2 anti-correlates with glioma patient survival.

Figure 6A:
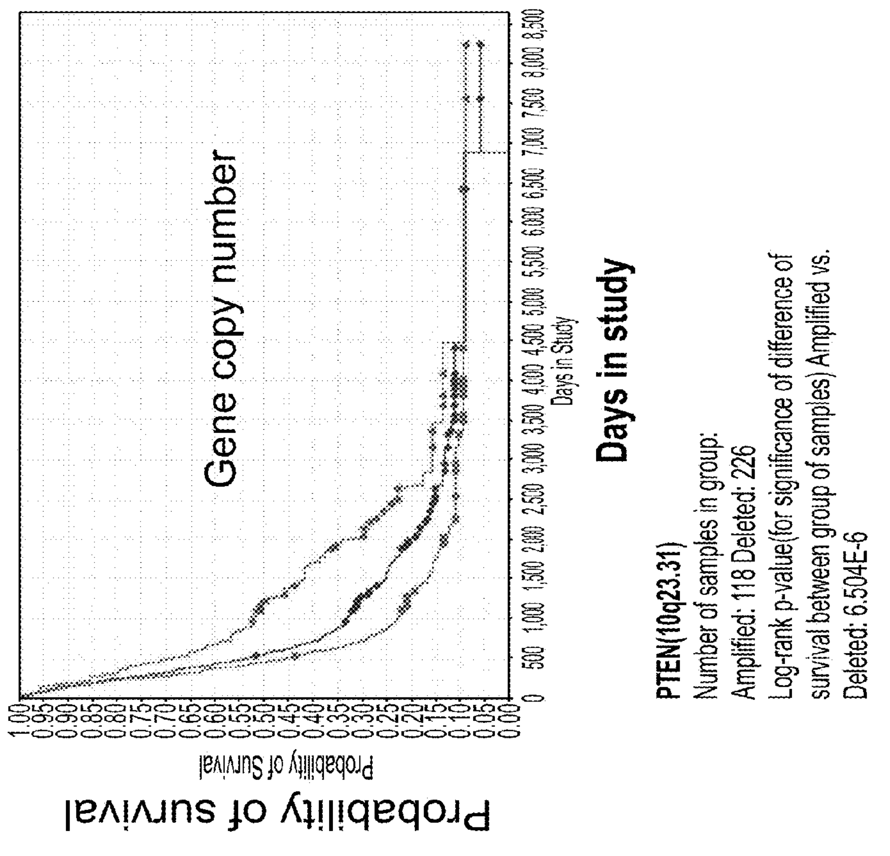

(FIG. 6A). Kaplan-Meier plots show the correlation between PTEN gene copy number and glioma patient survival. Samples with gene amplification (red line) n=118. Samples with gene deletion (green line) n=226. Blue line represents the survival of all glioma patients. Log-rank p-value (Amplified vs. Deleted): 6.504E-6. Data based on the National Cancer Institute REMBRANDT data set.

Figure 6B:
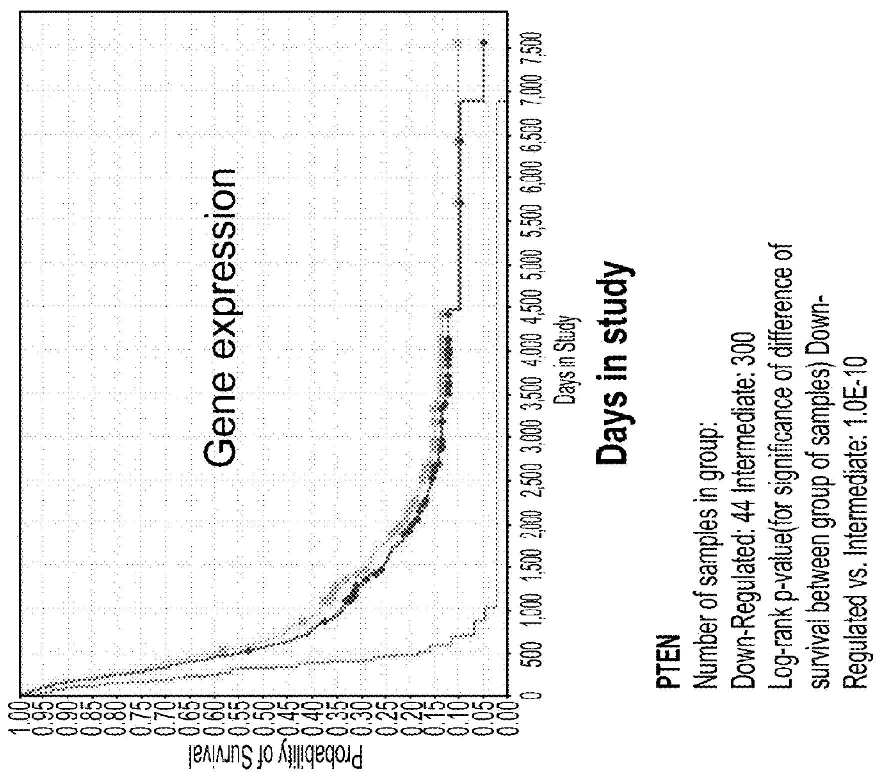

(FIG. 6B). Kaplan-Meier survival plots show the survival of glioma patients with differential expression of PTEN: Samples with Down-regulation (green line) n=44. Samples with intermediate expression (yellow) n=300. The blue line represents the survival of all glioma patients. Log-rank p-value (Down-regulated vs. Intermediate): 1.0E-10. Data based on the National Cancer Institute REMBRANDT data set.

Figure 6C:
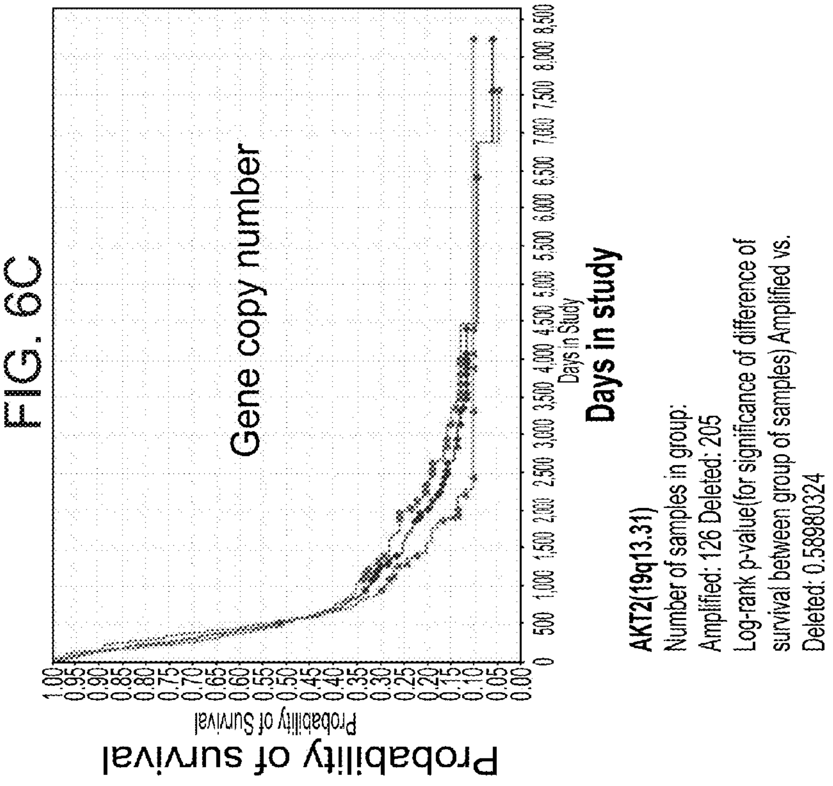

(FIG. 6C). Kaplan-Meier plots show the correlation between AKT2 gene copy number and glioma patient survival. Samples with gene amplification (red line) n=126. Samples with gene deletion (green line) n=205. Blue line represents the survival of all glioma patients. Log-rank p-value (Amplified vs. Deleted): 0.589. Data based on the National Cancer Institute REMBRANDT data set.

Figure 6D:
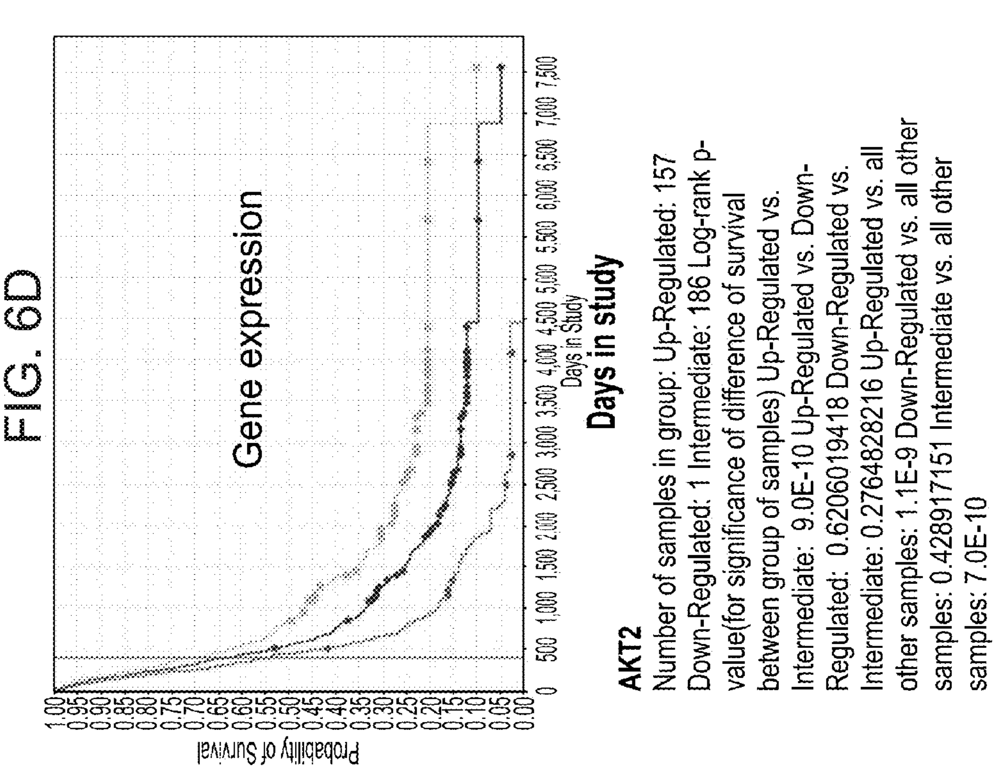

(FIG. 6D). Kaplan-Meier survival plots show the survival of glioma patients with differential expression of AKT2: Samples with up-regulation (red line) n=157. Samples with down-regulation (green line) n=1. Samples with intermediate expression (yellow) n=186. The blue line represents the survival of all glioma patients. Log-rank p-value (Up-regulated vs. Intermediate): 9.0E-10. Up-Regulated vs. all other samples: 1.1E-9. Intermediate vs. All other samples: 7.0E-10. Data based on the National Cancer Institute REMBRANDT data set.

Figure 7A:
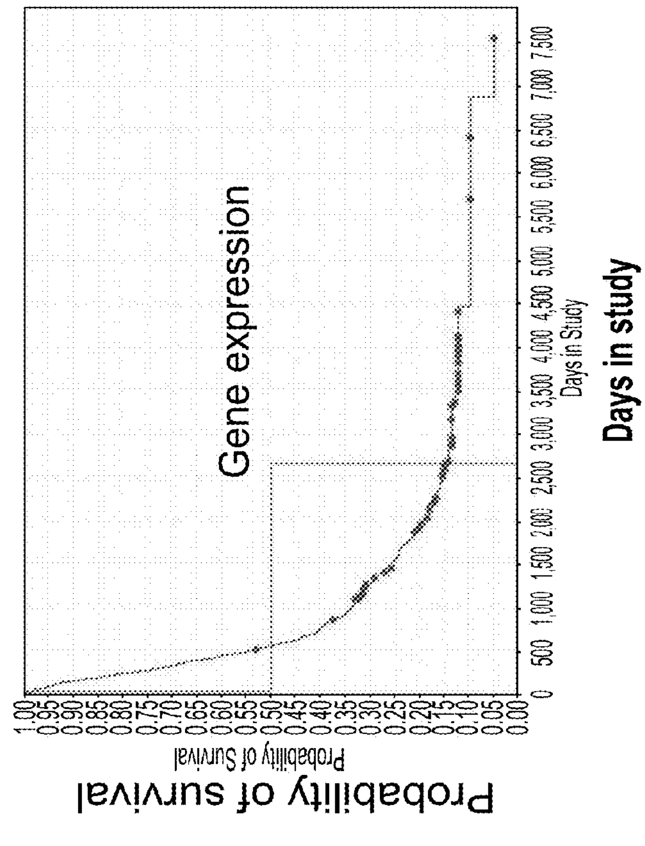
Figure 7B:
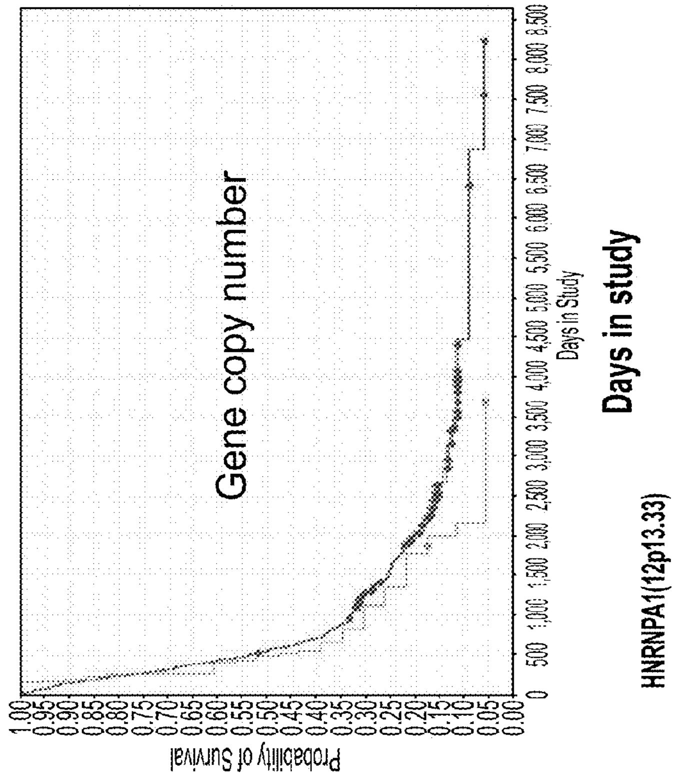
Figure 7C:
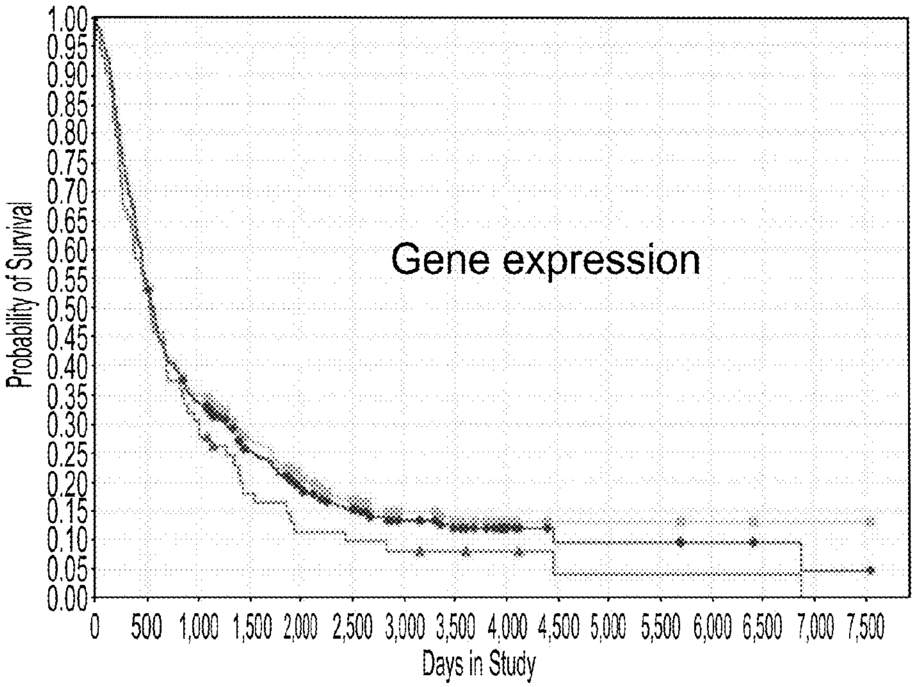

FIGS. 7A-C are Kaplan-Meier survival plots illustrating that gene copy number of hnRNP A1 and SF2/ASF expression do not correlate with glioma patient survival.

(A). Kaplan-Meier survival plots show the survival of glioma patients with differential expression of hnRNP A1: Samples with intermediate expression (yellow) n=342. Up-Regulated (red) n=2. The blue line represents the survival of all glioma patients. Log-rank p-value (for significance of difference of survival between group of samples) Up-Regulated vs. Intermediate: 0.9660533414. Data based on the National Cancer Institute REMBRANDT data set.

(FIG. 7B). Kaplan-Meier plots show the correlation between HNRNPA1 gene copy number and glioma patient survival. Samples with gene amplification (red line) n=321. Samples with gene deletion (green line) n=23. Blue line represents the survival of all glioma patients. Log-rank p-value (Amplified vs. Deleted): 0.4227139388. Data based on the National Cancer Institute REMBRANDT data set.

(FIG. 7C). Kaplan-Meier survival plots show the survival of glioma patients with differential expression of SF2/ASF: Samples with up-regulation (red line) n=72. Samples with intermediate expression (yellow) n=271. The blue line represents the survival of all glioma patients. Log-rank p-value (Upregulated vs. Intermediate): 0.1474297111. Data based on the National Cancer Institute REMBRANDT data set.

FIGS. 8A-J illustrate that hnRNP A2/B1 is required for of glioblastoma transformation.

(FIG. 8A). U87MG cells were transduced with retroviruses encoding hnRNP A2/B1-specific shRNA or empty vector (MLP(−)) and after selection cells were analyzed by Western blotting for hnRNP A2/B1 protein expression. β-catenin levels were used as loading control.

(FIG. 8B). Quantification of colony formation in soft agar of cells described in (A). Error bars represents standard deviations (n=2).

(FIG. 8C). Representative fields of colonies in soft agar described in (FIG. 8B).

(FIG. 8D). Cell proliferation of cells described in (FIG. 8A) was determinate by methylen blue staining. Error bars represents standard deviations (n=6).

Figure 8E:
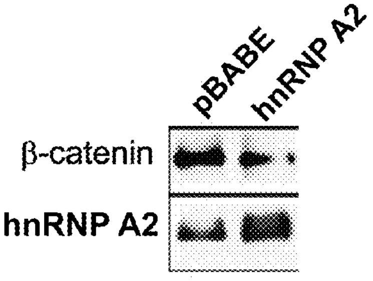

(FIG. 8E). U87MG cells transduced with empty vector (pBABE) or hnRNP A2/B1 (A2) were analyzed by Western blotting for hnRNP A2/B1 protein expression and β-catenin was used as loading control.

Figure 8F:
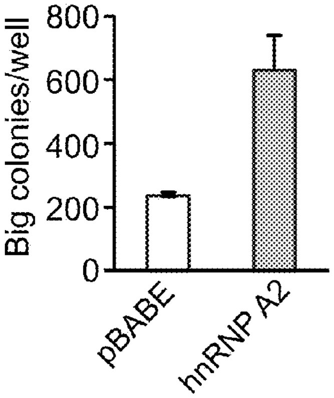

(FIG. 8F). Quantification of colony formation in soft agar of the cells described in (FIG. 8E). Colonies were considered "Big colonies" if the contained approximately over 100 cells or were over 1 mm in diameter. Error bars indicate standard deviations (n=2).

Figure 8G:
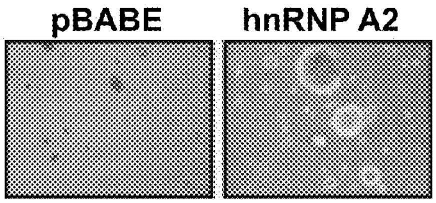

(FIG. 8G). Representative fields of soft agar colonies described in (FIG. 8F).

Figure 8H:
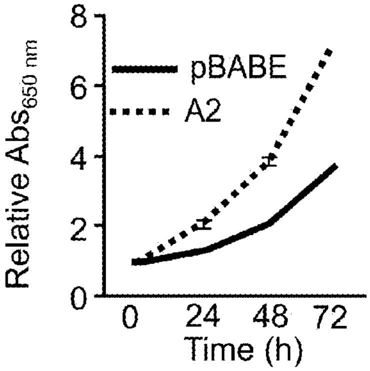

(FIG. 8H). Cell proliferation of cells described in (FIG. 8E) was determinate by methylen blue staining. Error bars represents standard deviations (n=6).

Figure 8I:
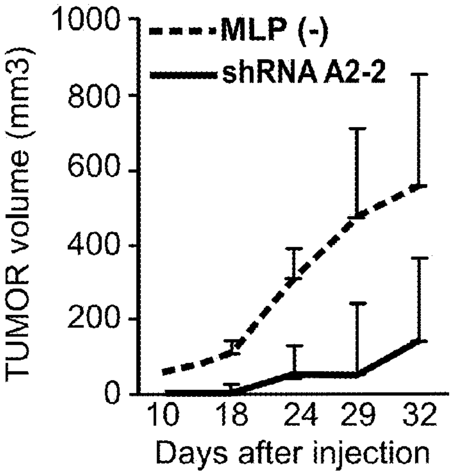

(FIG. 8I). Cells described in (FIG. 8A) were injected ($10^6$ cells/site) subcutaneously near both rare flanks of nude/nude mice, and tumor volume was measured bi-weekly. Error bars indicate standard deviations (n=8).

Figure 8J:
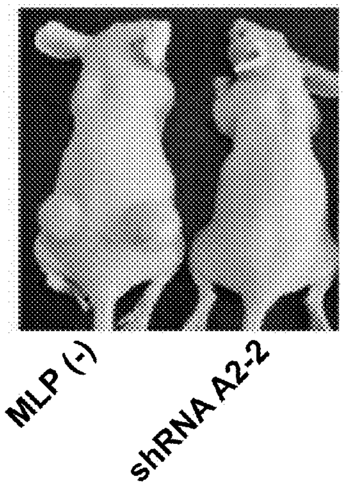

(FIG. 8J). Representative mice described in (FIG. 8I) are shown.

Figure 9A:
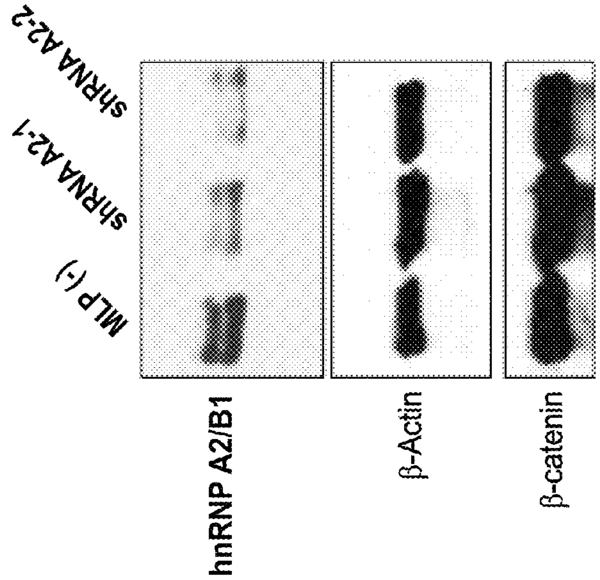
Figure 9B:
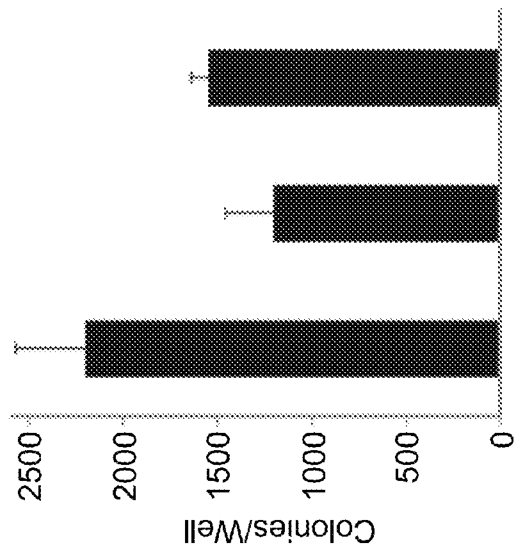
Figure 9C:
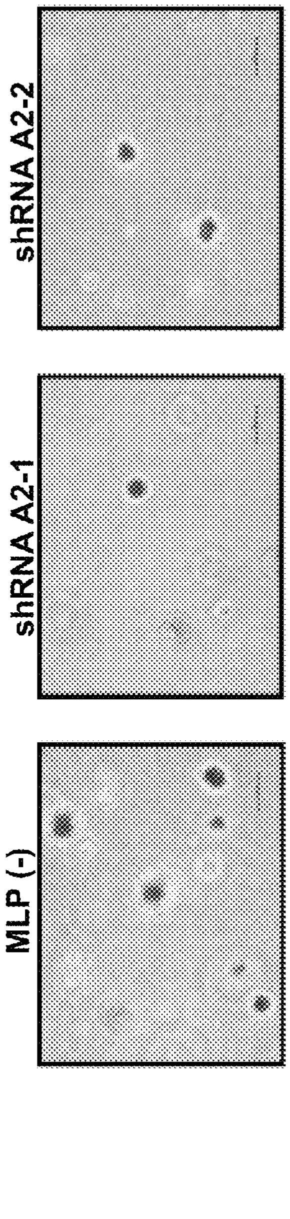

FIGS. 9A-C are photographs and graphs illustrating that hnRNP A2/B1 is required for of glioblastoma transformation.

(FIG. 9A). T98G cells were transduced with retroviruses encoding hnRNP A2/B1-specific shRNAs or empty vector (MLP(−)) and after selection cells were analyzed by Western blotting for hnRNP A2/B1 protein expression. β-actin and β-catenin levels were used as loading control. (FIG. 9B). Quantification of colony formation in soft agar of cells described in (FIG. 9A). Error bars represents standard deviations (n=2). (FIG. 9C). Representative fields of colonies in soft agar described in (FIG. 9B).

Figure 10A:
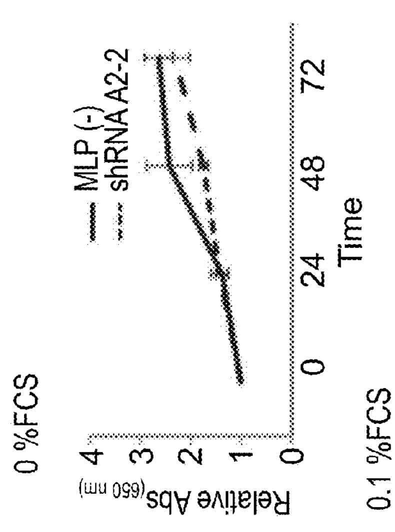
Figure 10B:
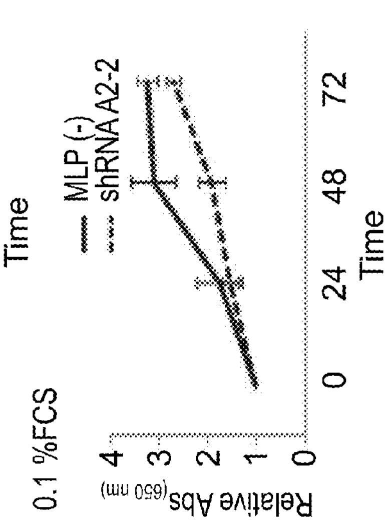
Figure 10C:
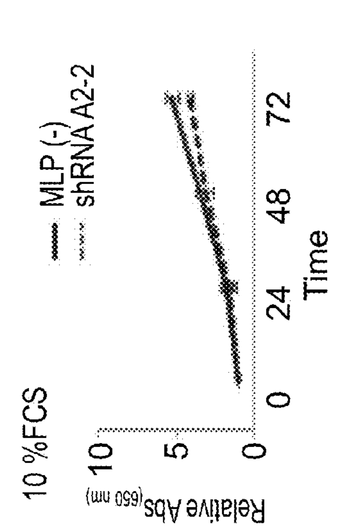
Figure 10D:
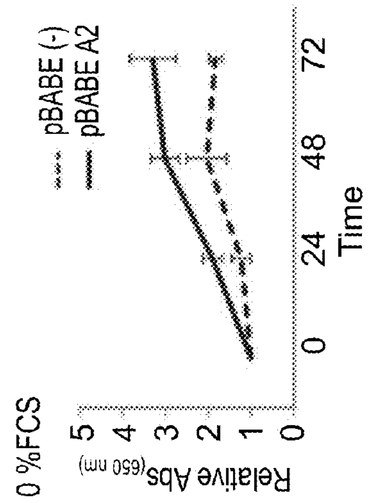
Figure 10E:
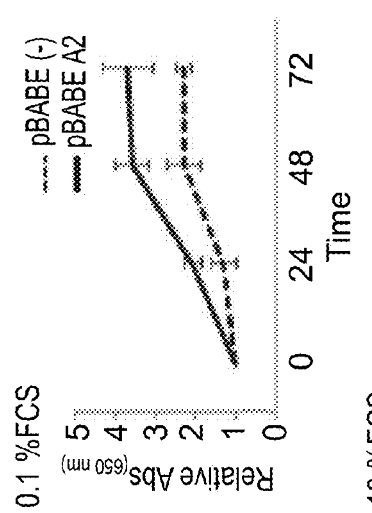
Figure 10F:
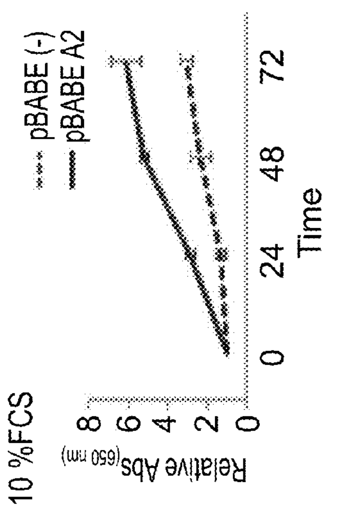
Figure 10H:
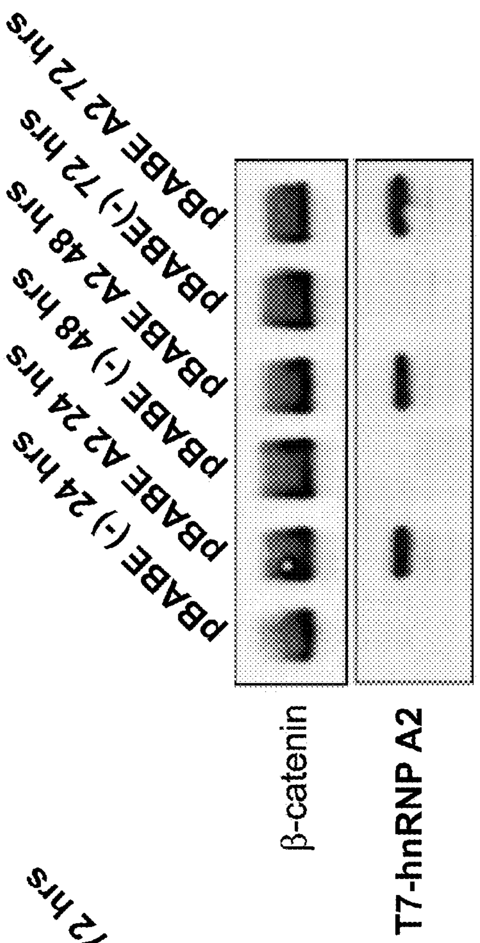
Figure 10G:
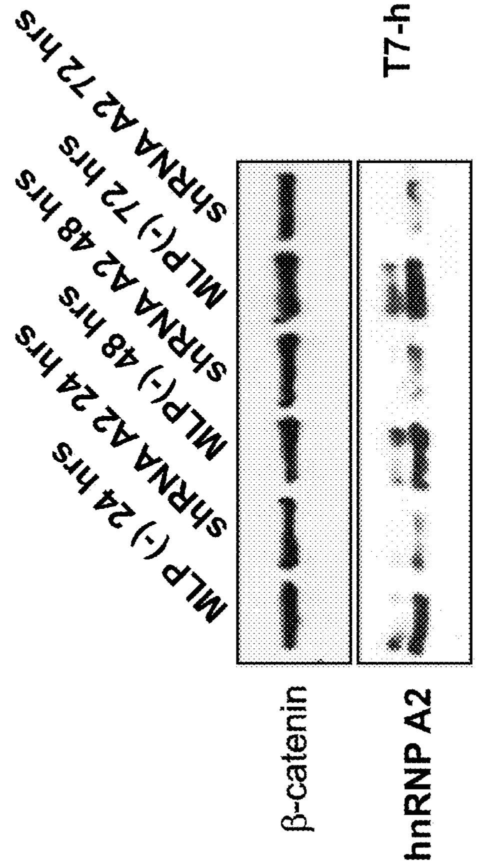

FIGS. 10A-H are graphs illustrating that hnRNP A2/B1 contributes to cell proliferation. Cell proliferation of U87MG cells transduced with retroviruses encoding hnRNP A2/B1-specific shRNA or empty vector (MLP(−)), at different serum conditions was determinate by methylen blue staining (FIGS. 10A, B and C). Error bars represents standard deviations (n=4). Cell proliferation of U87MG cells transduced with empty vector (pBABE) or hnRNP A2/B1 (A2) at different serum conditions was determinate by methylen blue staining (FIGS. 10D, E and F). Error bars represents standard deviations (n=4). (FIG. 10G). During cell growth U87MG cells transduced with retroviruses encoding hnRNP A2/B1-specific shRNA or empty vector (MLP(−)) were analyzed by Western blotting for hnRNP A2/B1 protein expression at 24, 48 and 72 hours of culturing. β-catenin was used as loading control. (FIG. 10H). During cell growth U87MG cells transduced with empty vector (pBABE) or hnRNP A2/B1 (A2) were analyzed by Western blotting for hnRNP A2/B1 protein expression at 24, 48 and 72 hours of culturing. β-catenin was used as loading control.

FIGS. 11A-G illustrate that hnRNP A2/B1 can transform NIH 3T3 cells in vitro and in vivo.

(FIG. 11A). NIH 3T3 cells transduced with empty vector (pBABE) or hnRNP A2/B1 (A2) were analyzed by Western blotting for hnRNP A2/B1 protein expression and β-catenin was used as loading control.

(FIG. 11B) Quantification of colony formation in soft agar of cells described in (FIG. 11A). Error bars represents standard deviations (n=2).

(FIG. 11C). Representative fields of colonies in soft agar described in (FIG. 11B).

(FIG. 11D). Proliferation of cells described in (FIG. 11A) was determinate by methylen blue staining. Error bars indicate the standard deviation (n=6).

(FIG. 11E). Cells described in (FIG. 11A) were injected ($10^6$ cells/site) subcutaneously near both rare flanks of nude/nude mice, and tumor volume was measured bi-weekly. Error bars indicate standard deviations (n=8).

(FIG. 11F). Representative mice described in (FIG. 11E) are shown.

(FIG. 11G). Light micrographs of formalin-fixed, paraffin-embedded tissue sections from tumors derived from NIH 3T3 cells overexpressing hnRNP A2/B1, stained with hematoxylin and eosin.

FIGS. 12A-H are graphs illustrating that hnRNP A2/B1 regulates the alternative splicing of tumor suppressors and oncogenes.

U87MG glioblastoma cancer cells were transduced with retroviruses encoding shRNA empty vector (MLP), or hnRNP A2/B1 specific shRNA, the empty pBABE vector or pBABE containing hnRNP A2/B. After selection cells were lysed, RNA isolated and the alternative splicing pattern of RON, INSR, ENAH, CFLAR, BIN, CASP9 and WWOX was examined by RT-PCR using the indicated isoform-specific primers (arrowheads). The splice variants are indicated by boxes at the right side of each gel. (FIG. 12A) RON exon 11 skipping/inclusion. (FIG. 12B) INSR exon 11 skipping/inclusion. (FIG. 12C) ENAH exon 11a skipping/inclusion. (FIG. 12D) CFLAR exon 7 skipping/inclusion. (FIG. 12E) BIN1 exons 12a and 13 skipping/inclusion. (FIG. 12F) CASP9 exons 3-6 skipping/inclusion. (FIG. 12G) WWOX exons 6-8 skipping/inclusion. (FIG. 12H) GAPDH control. Numbers under each panel represents the average and standard deviations of fold change in the inclusion of the indicated exon compared to the empty vectors (normalized as 1) in 2-4 independent experiments.

Figure 13A:
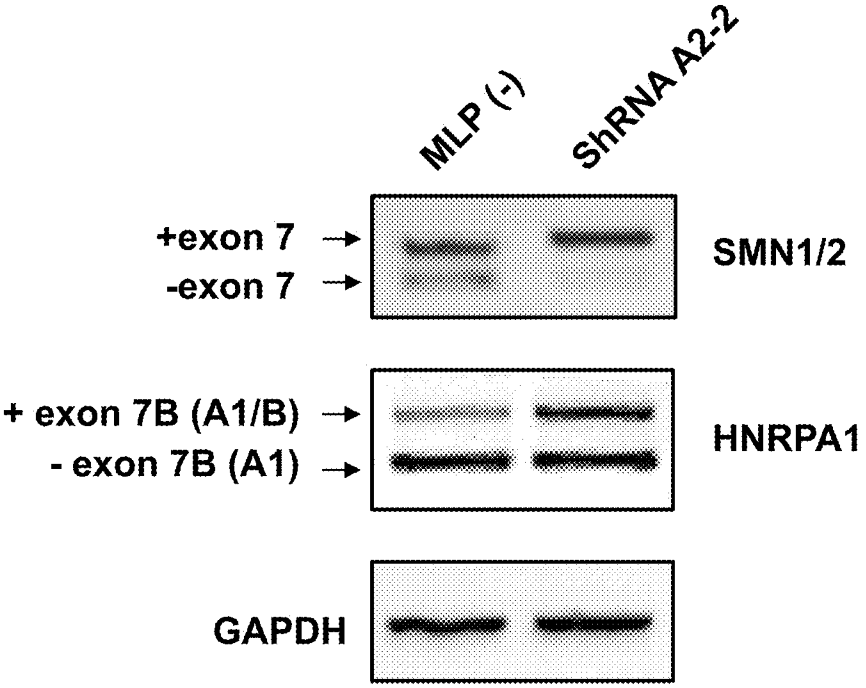
Figure 13B:
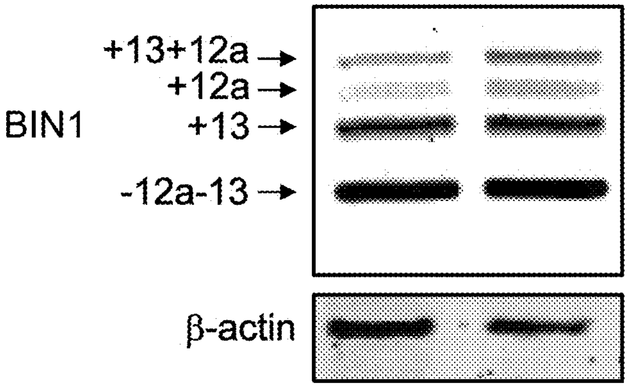

FIGS. 13A-B illustrate that hnRNP A2/B1 down-regulation increased the inclusion of hnRNP A1 exon 7B and exon 7 of the SMN gene.

(FIG. 13A). U87MG glioblastoma cancer cells were transduced with retroviruses encoding shRNA empty vector (MLP), or hnRNP A2/B1 specific shRNA. After selection cells were lysed, RNA isolated and the alternative splicing pattern of HNRPA1 and SMN genes was determined by RT-PCR.

(FIG. 13B). NIH-3T3 cells U87MG transduced with empty vector (pBABE) or hnRNP A2/B1 (A2). After selection cells were lysed, RNA isolated and the alternative splicing pattern of BIN was determined by RT-PCR. Beta actin was used as control.

Figure 14:
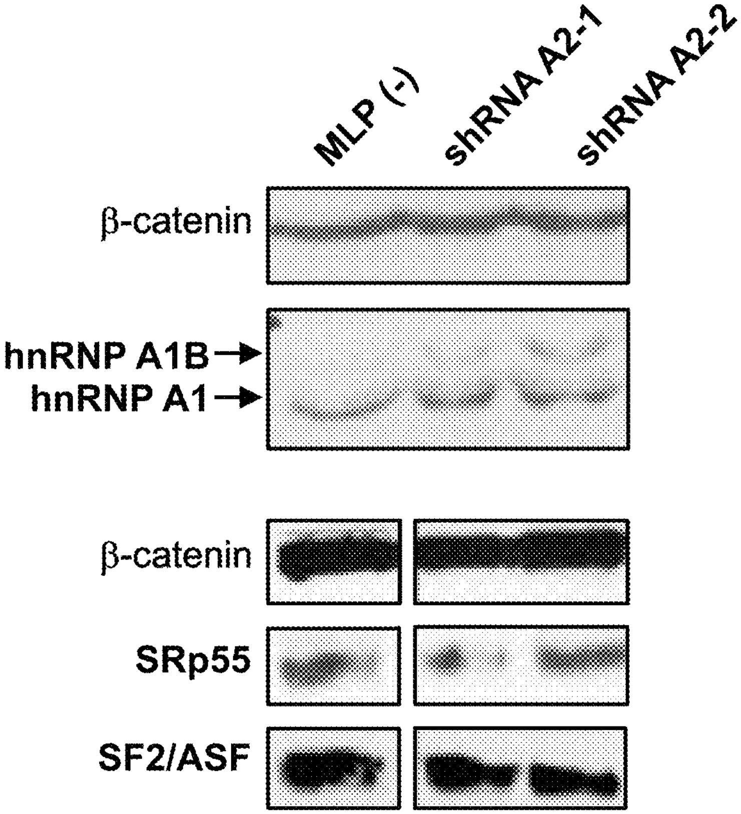

FIG. 14 illustrates that hnRNP A2/B1 down-regulation did not change the protein levels of SRSF1(SF2/ASF), SRSF6 (SRp55) and hnRNP A1. Western blot using specific antibodies to SRSF1 (SF2/ASF), SRSF6 (SRp55) and hnRNP A1 in lysates from U87MG cells transduced with the indicated retroviruses.

Figure 15A:
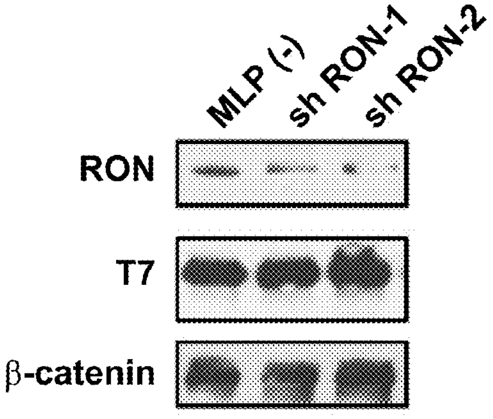
Figure 15B:
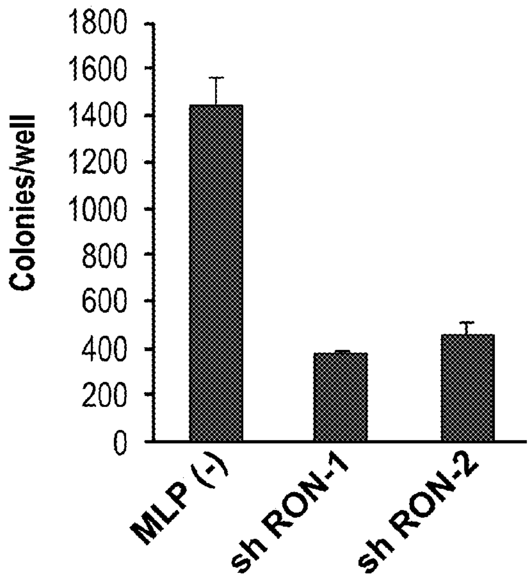
Figure 15C:
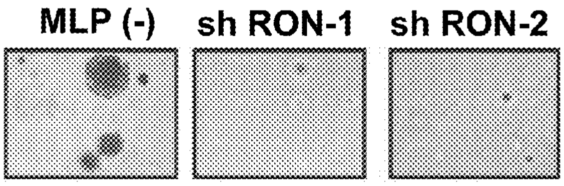

FIGS. 15A-C illustrate that knockdown of RON reverses transformation of U87MG cells overexpressing hnRNP A2.

U87MG cells transduced with hnRNP A2 cDNA were co-transduced with the indicated lentiviruses containing shRNAs against RON or an empty vector. After selection cells were plated into soft agar and 14 days later colonies were counted. (FIG. 15A) Western blot showing RON levels in the different cell populations. (FIG. 15B) Quantitation of colonies formed in soft agar from cells described in (FIG. 15A). (FIG. 15C) Representative fields of cells described in (FIG. 15A) (magnification ×10).

DESCRIPTION OF SPECIFIC EMBODIMENTS OF THE INVENTION

The present invention, in some embodiments thereof, relates to methods of diagnosing and treating cancer and, more specifically breast cancer and brain cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

An emerging body of data shows that alternative splicing misregulation plays an important role in cancer development and tumor maintenance. Alternative splicing regulators from the SR and hnRNP A/B protein families are overexpressed or down-regulated in various cancers and can probably account for many of the cancer-specific alternative splicing changes. Some alternative splicing regulators such as the SR protein SRSF1 (SF2/ASF) have been shown to be up-regulated in many cancers and act as potent oncogenes when slightly overexpressed (Karni et al., Nat Struct Mol Biol 2007; 14: 185-93).

However, to date there is no direct evidence that any member of the hnRNP A/B families is an oncogene that can transform cells and is genetically up-regulated (amplified, translocated or mutated) in cancer.

The present inventors compared breast primary tumor samples with metastatic effusions from different clinical stages of breast cancer and showed that the splicing factor hnRNP A2/B1 is over-expressed in advanced stages of breast cancer and in metastatic effusions (FIGS. 1A-C). The elevated levels of hnRNP A2/B1 was specific since they did not detect any change in the expression level of other splicing factors from the hnRNP A/B and SR protein families. Concomitantly with hnRNP A2/B1 overexpression, a significant change in the alternative splicing of many genes involved in motility and invasion were detected in breast metastatic effusions compared to primary tumors raising the hypothesis that there is a major change in the splicing pattern in breast metastatic effusions compared to primary tumors which is driven by hnRNP A2/B1 overexpression. Knockdown of hnRNP A2/B1 in the metastatic breast cancer cell line MDA-MB-231 induced inhibition of tumor growth in nude mice as well as inhibition of their metastasis to the lungs (FIGS. 2A-C).

Based on these results, the present inventors suggest that hnRNP A2/B1 is both a marker for the metastatic stage of breast cancer and for patient prognosis and tumor stage and is a putative oncogene in breast cancer. The present inventors found that several splicing targets of hnRNP A2/B1 change their isoform distribution upon knockdown or overexpression of hnRNP A2/B1 and suggest that hnRNP A2/B1 levels controls the splicing program of a large set of target genes which enhance invasiveness and other metastatic properties of breast cells. Accordingly, the present inventors propose that the splicing signature of hnRNP A2/B1 targets and/or hnRNP A2/B1 levels may serve as an accurate indication for metastasis of breast tumors and prognosis.

Figure 3B:
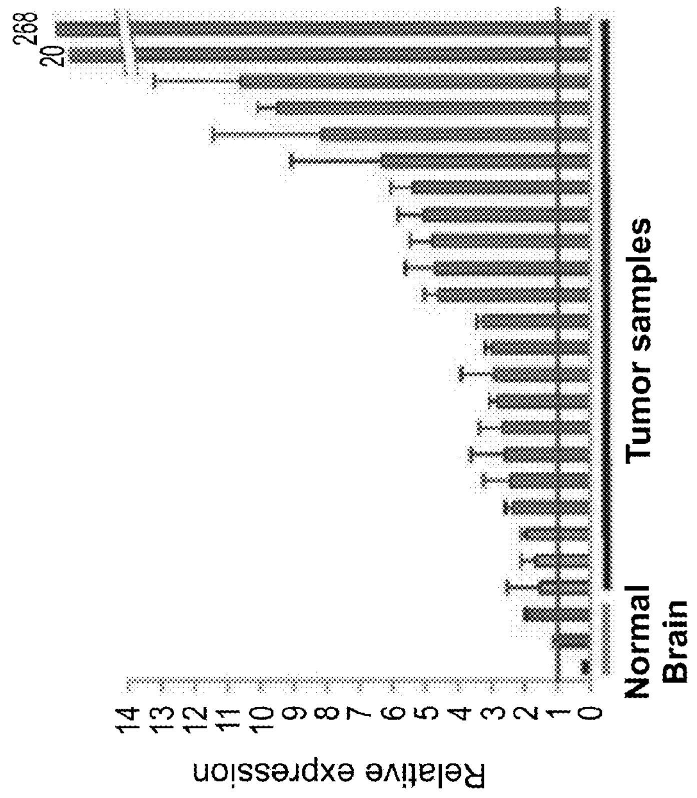
Figure 3A:
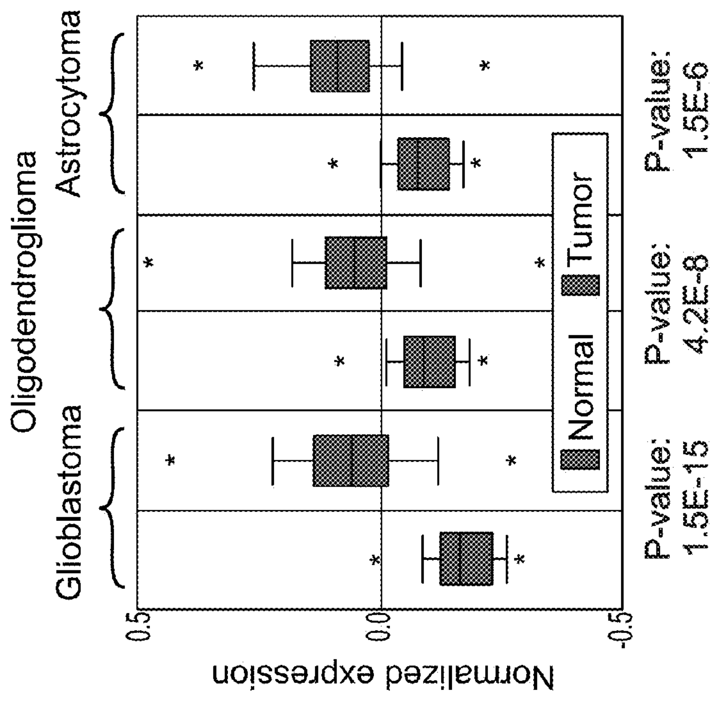
Figures 3C, 3D:
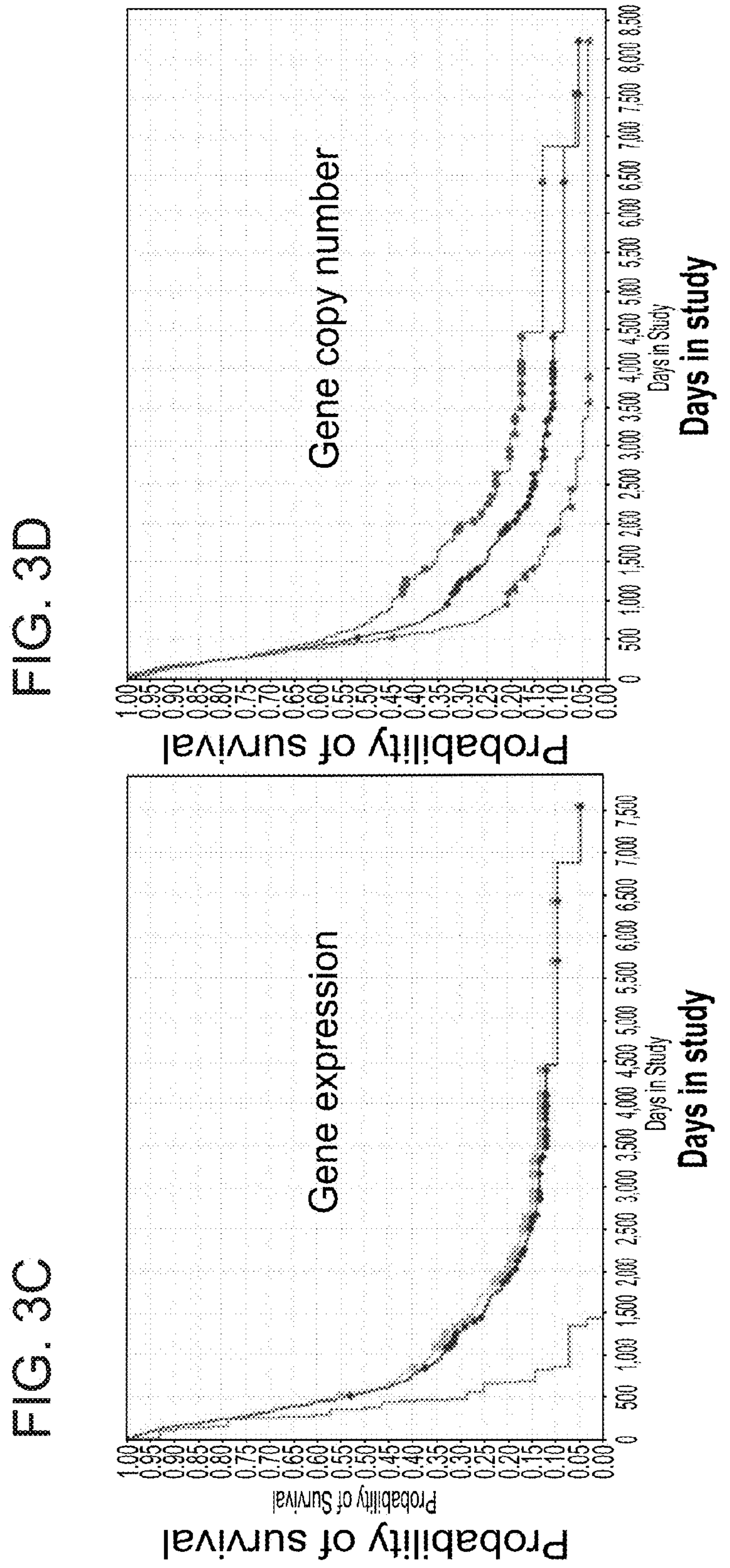

Whilst further reducing the present invention to practice, the present inventors compared expression of hnRNP A2/B1 in gliomas with normal brain samples and found that in the glioma samples there was amplification of the HNRPA2B1 gene (FIGS. 3A-D). Moreover, overexpression and amplification of hnRNP A2/B1 correlates with poor prognosis of glioma patients while deletion of the HNRPA2B1 gene correlates with better prognosis then average (FIGS. 3C-D). Importantly, none of the other hnRNP A/B proteins, as well as the SR proteins or some other known oncogenes, showed significant inverse correlation with survival of glioma patients (FIGS. 4A-D; FIGS. 5A-D). Taken together these findings suggest that hnRNP A2/B1 is a valuable prognostic marker for glioblastoma development and patient survival.

In order to examine if hnRNP A2/B1 is causatively involved in glioblastoma tumor development, the present inventors down-regulated the expression of hnRNP A2/B1. Knockdown of hnRNP A2/B1 in U87MG glioblastoma cells partially inhibited their proliferation, especially in low-serum condition (FIG. 8D; FIG. 10) and inhibited colony formation in soft agar as well as tumor formation in nude mice of glioblastoma cells (FIGS. 8A-C, FIGS. 8I-J, FIGS. 9A-C) suggesting that hnRNP A2/B1 is important for glioblastoma tumor development and maintenance. Moreover, overexpression of hnRNP A2/B1 in the U87MG glioblastoma cells enhanced their proliferation in all serum concentrations, and increased colony size and number in soft agar (FIGS. 8E-H, FIG. 10). To examine if hnRNP A2/B1 acts as an oncogene, the present inventors overexpressed (two fold) hnRNP A2/B1 in immortal mouse fibroblasts (NIH 3T3 cells) and examined their oncogenic properties. NIH 3T3 overexpressing hnRNP A2/B1 became transformed, formed colonies in soft agar and were tumorigenic in nude mice forming tumors with hallmarks of high grade sarcomas (FIGS. 11A-F). These data suggest that hnRNP A2/B1 acts as a proto-oncogene when slightly up-regulated and thus it is not only a marker but also a driving oncogene in glioblastoma development. In order to identify possible alternative splicing targets of hnRNP A2/B1 that might mediate its oncogenic activity, the alternative splicing pattern of several genes known to undergo alternative splicing in cancer and to contribute to the transformed phenotype were examined. Several alternative splicing events modulated by hnRNP A2/B1 were identified, among them the tumor suppressor BIN1, the anti apoptotic gene CFLAR (c-Flip) and CASP9 all regulators of the apoptotic process. These results suggest that hnRNP A2/B1 activates an alternative splicing program that enhances the production of anti apoptotic isoforms of genes such as BIN1, CASP9 and CFLAR as well as invasion-promoting isoforms such as ΔRON, CFLAR-long and IR-A which contribute to transformation and invasion.

In order to examine if RON is an important target that mediated hnRNP A2-induced transformation, the present inventors stably knocked down RON in U87MG glioblastoma cells overexpressing exogenous hnRNP A2 cDNA and found that RON knockdown significantly inhibited transformation of these cells similarly to the effect of hnRNP A2/B1 knockdown (FIGS. 15A-C).

Taken together the present data suggest that hnRNP A2/B1 is a new bio-marker for glioblastoma patient survival and a new proto-oncogene that regulate the splicing and other RNA processing steps of several tumor suppressors and oncogenes. Furthermore, the present inventors propose that down-regulating hnRNP A2/B1 levels in glioblastoma cells should be considered as a new strategy for glioblastoma therapy.

Thus, according to one aspect of the present invention, there is provided a method of diagnosing a metastatic breast cancer or a glioma in a subject in need thereof, the method comprising analyzing an amount or activity of heterogeneous nuclear ribonucleoprotein A2/B1 (hnRNP A2/B1) in a cell sample of the subject, wherein an up-regulation in an amount or activity of hnRNP A2/B1 beyond a predetermined threshold with respect to a control cell sample is indicative of the metastatic breast cancer, glioblastoma, oligodendrogioma or astrocytoma.

The term "diagnosing" as used herein refers to determining the presence of a disease, classifying a disease, staging a disease, determining a severity of a disease, monitoring disease progression, forecasting an outcome of the disease, predicting survival and/or prospects of recovery (i.e. prognosis).

The subject may be a healthy animal or human subject undergoing a routine well-being check up. Alternatively, the subject may be at risk of having cancer (e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). Still alternatively, the subject may be diagnosed as having the cancer, but the stage is being evaluated.

The term "predicting metastasis" as used herein refers to determining the presence of metastasis either prior to the event of metastasis or following the event of metastasis i.e. diagnosing.

As used herein, the term "metastatic breast cancer" refers to a disease in which at least one transformed, i.e. cancerous cell from a primary tumor of the breast has become separated from the primary tumor and has continued to grow into a tumor at a location distinct from that of the primary tumor (hereinafter "distinct location"). The distinct location may for example be within the same breast as that in which the primary tumor is located (ipsilateral breast) or within the other breast (contralateral breast). As further examples, the distinct location may be within one or more lymph nodes, whether these are movable or fixed, ipsilateral or contralateral to the primary tumor, supraclavicular, axillary or otherwise. Within the context of the TNM tumor classification system, a "metastatic breast cancer" would include all tumors whose staging includes M=1 (i.e. Stage 1V breast cancer), i.e. all tumors for which any degree of metastasis exists to distant locations such as for example lung, liver, bone, lymph nodes, skin, brain and/or a distinct location within an ipsilateral and/or contralateral breast.

It should be noted that the term "metastatic breast cancer" does not imply that the metastasis existing at a "distinct location" must have arisen from any one particular primary tumor of the breast. That is to say, the origin of the metastasis at the "distinct location" is immaterial to the designation of the disease as "metastatic breast cancer" as long as the primary tumor giving rise to the metastasis originated in the breast tissue. For this purpose, the term "breast tissue" is to be understood as including the lobules and the ducts of the breast, i.e. the tissue which most commonly gives rise to tumors of the breast.

Gliomas are a diverse group of brain tumors that arise from normal "glial" cells of the brain and/or their precursor cells. The most important determinant of survival for gliomas is the "grade" of the glioma. Secondary determinants of survival are age at diagnosis, performance status, and extent of surgery. Patients with low-grade gliomas have a protracted natural history with generally long survival times, while those with high grade gliomas are much more difficult to successfully treat and have shorter survival times. All gliomas have specific signs and symptoms that are primarily related to the location and size of the glioma.

The temporal lobe gliomas, for example, may cause seizures, difficulty with speech and/or loss of memory. The frontal lobe gliomas may cause seizures, behavioral changes, weakness of the arms or legs on the opposite side of the body, and/or difficulty with speech. The occipital gliomas may cause loss of vision. The parietal gliomas may cause loss of spatial orientation, diminished sensation on the opposite side of the body, and/or inability to recognize once familiar objects or persons.

Astrocytomas are glioma tumors that arise from brain cells called astrocytes or their precursors. Astrocytes are cells in the central nervous system that support neuronal function. Astrocytomas can be graded by histologic features that signify increasing malignancy into astrocytoma, anaplastic astrocytoma, or glioblastoma multiforme. Anaplastic astrocytoma and glioblastoma multiforme are considered high-grade gliomas while the astrocytoma is considered to be a low-grade glioma. High-grade tumors grow rapidly and can easily infiltrate and spread through the brain. Low-grade astrocytomas can also infiltrate the brain but are usually more localized and grow slowly over a long period of time. High-grade tumors are much more aggressive and require very intense therapy. The majority of astrocytic tumors in children are low-grade, whereas the majority in adults are high-grade. Astrocytomas can occur anywhere in the brain and spinal cord, however the majority are located in the cerebral hemispheres (the top part of the brain).

Oligodendrogliomas are also gliomas. They arise from oligodendrocytes and/or their cell precursors. Normal oligodendrocytes provide myelin, a fatty substance that covers nerve axons in the brain and spinal cord and allows nerves to conduct electrical impulses more efficiently. Oligodendrogliomas are classified as low grade oligodendroglioma (less aggressive) and anaplastic oligodendroglioma (more aggressive). More common than pure oligodendrogliomas are low grade and anaplastic tumors that are a mixture of astrocytoma and oligodendroglioma ("oligoastrocytomas").

As mentioned, diagnosis of the above diseases is effected by analyzing an expression of hnRNP A2/B1.

As used herein, the term "heterogeneous nuclear ribonucleoprotein A2/B1 (hnRNP A2/B1)" refers to the expression product (either RNA or protein) of the human gene located at chromosomal location 7p15 (gene ID 3181).

This gene belongs to the A/B subfamily of ubiquitously expressed heterogeneous nuclear ribonucleoproteins (hnRNPs). The hnRNPs are RNA binding proteins and they complex with heterogeneous nuclear RNA (hnRNA). These proteins are associated with pre-mRNAs in the nucleus and appear to influence pre-mRNA processing and other aspects of mRNA metabolism and transport. The protein encoded by this gene has two repeats of quasi-RRM domains that bind to RNAs. This gene has been described to generate two alternatively spliced transcript variants which encode different isoforms [NM_002137—SEQ ID NO: 55 and NM_031243.2—SEQ ID NO: 56]. Variant (B1) contains an additional 36 bases compared to variant A2. This additional region affects only the beginning of the coding region. The N-terminus of isoform B1 is thus different from isoform A2.

Determining an expression of hnRNP A2/B1 may be effected on the RNA or protein level as detailed below.

Methods of Detecting Expression of hnRNP A2/B1 on the RNA Level

In order to detect expression of hnRNP A2/B1 on the RNA level, typically polynucleotide probes (e.g. oligonucleotides or primers) are used that are capable of specifically hybridizing with nhRNP A2/B1 RNA or cDNA generated therefrom.

Preferably, the oligonucleotide probes and primers utilized by the various hybridization techniques described hereinabove are capable of hybridizing to the hnRNP A2/B1 under stringent hybridization conditions.

By way of example, hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMAC1, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1-1.5° C. below the Tm, final wash solution of 3 M TMAC1, 0.01 M sodium phosphate (pH 6.8), 1 mM EDTA (pH 7.6), 0.5% SDS at 1-1.5° C. below the Tm (stringent hybridization conditions) (ii) hybridization solution of 6×SSC and 0.1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2-2.5° C. below the Tm, final wash solution of 3 M TMAC1, 0.01 M sodium phosphate (pH 6.8), 1 mM EDTA (pH 7.6), 0.5% SDS at 1-1.5° C. below the Tm, final wash solution of 6×SSC, and final wash at 22° C. (stringent to moderate hybridization conditions); and (iii) hybridization solution of 6×SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature at 2.5-3° C. below the Tm and final wash solution of 6×SSC at 22° C. (moderate hybridization solution).

It will be appreciated that in order to avoid detection of only one of the two isoforms of hnRNP A2/B1, it is preferable that the polynucleotide probe/primer hybridizes with hnRNP A2/B1 at a nucleic acid sequence which is shared by the two isoforms.

Below is a list of techniques which may be used to detect hnRNP A2/B1 on the RNA level.

Northern Blot Analysis:

This method involves the detection of a particular RNA i.e. hnRNP A2/B1 RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide Microarray—

In this method oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Methods of Detecting hnRNP A2/B1 on the Protein Level

Determining expression of hnRNP A2/B1 on the protein level is typically effected using an antibody capable of specifically interacting with hnRNP A2/B1. Methods of detecting hnRNP A2/B1 include immunoassays which include but are not limited to competitive and non-competitive assay systems using techniques such as Western blots, radioimmunoassays, ELISA (enzyme linked immunosorbent assay), “sandwich” immunoassays, and immunoprecipitation assays and immunohistochemical assays as detailed herein below.

It will be appreciated that in order to avoid detection of only one of the two isoforms of hnRNP A2/B1, it is preferable that the antibody recognizes an epitope of hnRNP A2/B1 which is shared by the two isoforms.

Below is a list of techniques which may be used to determine the level of nRNP A2/B1 on the protein level.

Enzyme Linked Immunosorbent Assay (ELISA):

This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

It will be appreciated that the method of the present invention may also be performed by measuring an activity of hnRNP A2/B1. For example, the present inventors have shown that hnRNP A2/B1 over-expression correlates with skipping of exon 7B (A1B) of hnRNP A1. Accordingly, the present invention also contemplates analyzing the product of the hnRNP A1 gene as a gauge to determining the activity of hnRNP A2/B1.

As mentioned, the diagnosis/staging is carried out by analyzing an amount or activity of hnRNP A2/B1 in a cell sample of the subject, wherein a difference in an amount or activity of hnRNP A2/B1 beyond a predetermined threshold with respect to a control cell sample is indicative of the disease. The present inventors have shown that the expression level of hnRNP A2/B1 correlates with the progression of the disease. Thus, high expression levels indicate a later stage of the disease with a poorer prognosis, whereas low expression levels indicate an early stage of the disease with a better prognosis.

The cell sample may comprise cells of the primary tumor and/or metastatic effusion thereof. It will be appreciated that in the case of diagnosing/staging breast cancer, the cell sample typically comprises cells of the breast tumor and in the case of diagnosing/staging a glioma, the cell sample typically comprises cells of the glioma.

The control cell sample typically depends on the tumor cells being analyzed. Thus, in the case of breast cancer, the control sample may comprise breast cells of a healthy individual (or at least one not suffering from breast cancer) or from a known stage of breast cancer (e.g. non-metastatic stage). In the case of glioma, the control sample may comprise brain cells of a healthy individual (or at least one not suffering from brain cancer) or from a known stage of brain cancer.

The control cells are typically normally differentiated, non-cancerous cells, preferably of the same tissue and specimen as the tested cells suspicious of a cancerous or undifferentiated phenotype. Typically, the amount of change in expression of hnRNP A2/B1 is statistically significant.

Preferably, the difference is at least 10%, 20%, 30%, 40%, 50%, 80%, 100% (i.e., two-fold), 3 fold, 5 fold or 10 fold different as compared to the control cells.

It will be appreciated that the control data may also be taken from databases and literature.

On obtaining the results of the analysis, the subject is typically informed. Additional diagnostic tests may also be performed so as to corroborate the results of the diagnosing (e.g. gold standard tests, assessing the aggressiveness of the tumor, the patient's health and susceptibility to treatment, etc).

Imaging studies such as CT and/or MRI may be obtained to further diagnose the cancer/metastasis.

In addition, the diagnosis or choice of therapy may be determined by further assessing the size of the tumor, or the lymph node stage or both, optionally together or in combination with other risk factors. In the case of breast cancer for example, other factors which may of course be assessed for determining the choice of therapy may include receptor status, such as oestrogen receptor (ER) or progesterone receptor (PR) status, as known in the art. For example, the choice of therapy may be determined by further assessing the oestrogen receptor (ER) status of the breast tumor. In the case of gliomas, other factors which may be assessed include 1p/19q codeletion in oligodendroglial tumors, mutations in the isocitrate dehydrogenase 1 and 2 genes in diffuse gliomas, hypermethylation of the O(6)-methylguanine-DNA methyltransferase gene promoter in glioblastomas and anaplastic gliomas, alterations in the epidermal growth factor receptor and phosphatase and tensin homolog genes in high-grade gliomas, as well as BRAF alterations in pilocytic astrocytomas.

Suitably, the information obtained by the regarding may also be used by the clinician to recommend a suitable treatment, in line with the grade of the tumor which has been reassigned.

Thus, a tumor which has been reassigned to Grade 1 may require less aggressive treatment than a tumor which has been reassigned to Grade 3, for example. The present invention therefore includes a method of choosing a therapy for an individual with breast cancer, the method comprising assigning a grade to the breast tumor by a method as described herein, and choosing an appropriate therapy based on the aggressiveness of the breast tumor. In general, the method may be employed for the treatment of an individual with breast cancer, by assigning a grade to the breast tumor and administering an appropriate therapy to the individual based on the aggressiveness of the breast tumor.

Specifically, the choice of therapy may be determined by assessing the Nottingham Prognostic Index (NPI). The NPI is described in detail in Haybittle, et al., 1982. In combination with the grading methods described here, the method is suitable for assigning a breast tumor patient into a prognostic group. Such a combined method comprises deriving a score which is the sum of the following: (a) (0.2× tumor size in cm); (b) tumor grade in which the tumor grade is assigned by the method described herein; and (c) lymph node stage; in which the tumor size and the lymph node stage are determined according to the Nottingham Prognostic Index, in which a patient with a low score is categorized to a EPG (excellent prognostic group), a patient with a higher score is categorized to a GPG (good prognostic group), a patient with a still higher score is categorized to a MPG (moderate prognostic group), a patient with a score of a very high score is categorized to a PPG (poor prognostic group).

Alternatively, or in addition, a method of assigning a breast tumor patient into a prognostic group may comprise applying the Nottingham Prognostic Index to a breast tumor, but modified such that the histologic grade score of the breast tumor is replaced by a grade obtained by the method as described in this document.

It will be appreciated that the tools necessary for diagnosing cancer may be provided as a kit, such as an FDA-approved kit, which may contain one or more unit dosage form containing the active agent (e.g. antibody or probe) for detection of at least one marker of the present invention. The kit may be accompanied by instructions for administration. The kit may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration.

The present inventors showed that knock-down of hnRNP A2/B1 reduced the oncogenic properties of cancerous cells and further lowered the amount of metastasis of the cells.

Thus, according to another aspect of the present invention, there is provided a method of treating a metastasized breast cancer or glioma in a subject in need thereof, the method comprising administering to the subject a therapeutically effective amount of an agent which down-regulates an amount or activity of hnRNP A2/B1 or a target thereof.

Following is a list of agents capable of downregulating expression level and/or activity of HNRNP A2/B1.

One example, of an agent capable of downregulating HNRNP A2/B1 is an antibody or antibody fragment capable of specifically binding HNRNP A2/B1. Preferably, the antibody specifically binds at least one epitope of a HNRNP A2/B1. As used herein, the term "epitope" refers to any antigenic determinant on an antigen to which the paratope of an antibody binds.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Downregulation of HNRNP A2/B1 can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., HNRNP A2/B1) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl. Acad. Sci. USA. 2002; 99:1443-1448; Tran N., et al., FEBS Lett. 2004; 573: 127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi: 10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with some embodiments of the invention can be effected as follows. First, the HNRNP A2/B1 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambion.com/techlib/tn/91/912.html).

Second, potential target sites are compared to an appropriate genomic database (e.g., human, mouse, rat etc.) using any sequence alignment software, such as the BLAST software available from the NCBI server (wwwdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

Another agent capable of downregulating HNRNP A2/B1 is a DNAzyme molecule capable of specifically cleaving an mRNA transcript or DNA sequence of the HNRNP A2/B1. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

Downregulation of HNRNP A2/B1 can also be effected by using an antisense polynucleotide capable of specifically hybridizing with an mRNA transcript encoding HNRNP A2/B1. The antisense polynucleotide may be modified—e.g. PNA or LNA modified sequences.

Another agent capable of downregulating HNRNP A2/B1 is a ribozyme molecule capable of specifically cleaving an mRNA transcript encoding HNRNP A2/B1. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of HNRNP A2/B1 gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| | | | | |
|---|---|---|---|---|
| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Thus for any given sequence in the HNRNP A2/B1 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Another agent capable of downregulating HNRNP A2/B1 would be any molecule which binds to and/or cleaves HNRNP A2/B1. Such molecules can be HNRNP A2/B1 antagonists, or HNRNP A2/B1 inhibitory peptide.

In the case of breast cancer, the present inventors have noted that down-regulation of a target of hnRNP A2/B1 also is advantageous for the treatment of cancer. Thus, for example, the present invention contemplates down-regulation of hnRNP A1 (NM_002136.2—SEQ ID NO: 57, NM_031157.2—SEQ ID NO:58) for the treatment of cancer.

In the case of gliomas, the present inventors have noted that down-regulation of a target of hnRNP A2/B1 also is advantageous for the treatment of cancer. Thus, for example, the present invention contemplates down-regulation of macrophage stimulating 1 receptor (c-met-related tyrosine kinase), also known as RON (NM_002447.2—SEQ ID NO: 59) for the treatment of cancer.

Agents which specifically down-regulate hnRNP A1 or RON include those listed herein above for hnRNP A2/B1.

Selecting agents useful for treating metastasized brain cancer or glioma may be effected by contacting candidate agents with a population of cells (e.g. cancer cells) and analyzing an expression of hnRNP A2/B1, RON and/or hnRNP A1. Agents which are capable of decreasing expression of any of these markers are indicative for being useful for treating the above mentioned diseases.

The cancer cells may be primary cells (e.g. derived from a patient having the cancer) or may be immortalized cells (e.g. cell line). Contacting may be effected in vivo (e.g. in animal models), ex vivo or in vitro.

Once a candidate agent shows that it is capable of down-regulating expression of any of the above markers, anti-oncogenic potential thereof may be tested using other known in-vitro tests. The candidate agent's anti-oncogenic potential may also be tested in animal models for breast cancer and gliomas.

Once its anti-oncogenic potential has been corroborated, pharmaceutical compositions comprising same may be synthesized, as described herein below.

The agents used to down-regulate hnRNP A2/B1, hnRNP A1 and/or RON may be provided per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent which down-regulates hnRNP A2/B1, hnRNP A1 and/or RON, accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (hnRNP A2/B1, hnRNP A1 and/or RON) effective to prevent, alleviate or ameliorate symptoms of a disorder (e.g., metastatic breast cancer or glioma) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide blood or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

The Splicing Factor hnRNP A2/B1 in as a Diagnostic and Prognostic Marker for Metastatic Breast Cancer Results hnRNP A2/B1 Expression Correlates with Disease Stage of Breast Cancer Patients and it is Overexpressed in Metastatic Pleural Effusions Compared with Primary Breast Tumors The present inventors analyzed the Oncomine database (wwwdotworldwidewebdotoncominedotorg/) and found that hnRNP A2/B1 expression correlates with breast cancer disease progression in several experiments in a statistically significant manner (FIG. 1A). The present inventors also analyzed the expression of hnRNP A2/B1, hnRNP A1, SF2/ASF and SRp55 in primary breast tumors compared to metastatic effusions to the lungs and found that only hnRNP A2/B1 was overexpressed in the metastatic effusions (except of one patient which might have un-identified metastatic disease) (FIG. 1B and data not shown). hnRNP A2/B1 over-expression was detected also at the protein level (FIG. 1C). hnRNP A2/B1 over-expression correlated with skipping of exon 7B (A1B) of hnRNP A1 suggesting that this exon is a splicing target of hnRNP A2/B1. Indeed, knockdown of hnRNP A2/B1 showed a reciprocal change to enhance the inclusion of this exon (FIG. 2A). We detected many other splicing changes indicating that hnRNP A2/B1 affects a set of splicing events (data not shown).

Knockdown of hnRNP A2/B1 in the Metastatic Breast Cancer Cell Line MDA-MB-231 Inhibits Tumorigenesis and Metastasis into the Lungs The present inventors stably transduced the metastatic breast cancer cell line MDA-MB-231 which was labeled with GFP with retroviruses encoding for specific shRNA against hnRNP A2/B1 or hnRNP A1 (FIG. 2A). It was found that knockdown of hnRNP A2/B1 induces the inclusion of exon 7B of hnRNP A1 indicating that this exon is a splicing target of hnRNP A2/B1 (FIG. 2A). The effect of hnRNP A2/B1 knockdown was measured on cell proliferation but no significant effects on cellular proliferation were found (data not shown). The transduced pools of cells were injected into the flanks of nude mice and tumor growth and metastasis was followed into the lungs. It was found that knockdown of both hnRNP A2/B1 and hnRNP A1 inhibited tumor growth (FIG. 2B). After mice were sacrificed, lungs were taken out and visualized under a fluorescent dissecting scope to detect GFP-positive metastatic nodules in the lungs. As shown in FIG. 2C, metastatic nodules were detected only in cells expressing the empty vector but not in cells with hnRNP A2/B2 or Alknockdown (FIG. 2C).

Example 2 hnRNP A2/B1 Expression Level and Gene Copy Number as a Prognostic Marker for Glioma Patient Survival, Disease Stage and Severity Materials and Methods Cells:

U87MG and T98G cells were grown in DMEM, supplemented with 10% FCS, penicillin and streptomycin. NIH 3T3 cells were grown in DMEM supplemented with 10% calf serum (CS), penicillin, and streptomycin. To generate stable transductant pools, NIH 3T3 and U87MG cells were infected with pBABE-puro retroviral vectors expressing T7-tagged human hnRNP A2 cDNA. At 24 hours following infection, the medium was replaced, and 24 hours later, infected cells were selected with puromycin (2 μg/ml) for 72-96 hours. In the case of infection with MLP-puro-shRNAs vectors, U87MG, T98G cells transductants were selected with puromycin (2 μg/ml) for 96 hours.

Anchorage-Independent Growth:

Colony formation in soft agar was assayed as described (Karni et al., Proc Natl Acad Sci USA 2008; 105: 15323-7). Plates were incubated at 37° C. and 5% $CO_2$. After 14-21 days, colonies from 10 different fields in each of two wells were counted for each treatment, and the average number of colonies per well was calculated. The colonies were stained as described (Karni et al., Proc Natl Acad Sci USA 2008; 105:15323-7) and photographed under a light microscope at magnification ×100.

Tumorigenesis Assays in Nude Mice:

U87MG cells expressing MLP-puro or MLP-puro containing hnRNP A2 shRNAs or NIH 3T3 cells overexpressing hnRNP A2 or an empty vector (pBABE) were injected ($2\times10^6$ cells per site in 200 μl of PBS) s.c. into each rear flank of (Atimic-Nu/Nu) nude mice by using a 26-gauge needle. Tumor growth was monitored twice a week as described (Karni et al., Nat Struct Mol Biol 2007; 14: 185-93).

Immunoblotting:

Cells were lysed in SDS and analyzed for total protein concentration as described (Karni et al., Nat Struct Mol Biol 2007; 14:185-93). Thirty or 20 μg of total protein from each cell lysate was separated by SDS/PAGE and transferred onto a nitrocellulose membrane. The membranes were blocked and probed with antibodies by using enhanced chemiluminescence detection. Primary antibodies: anti β-catenin (1:2,000; Sigma); anti β-actin (1:2000 Santa Cruz); anti RON (1:1000 Santa Cruz); anti hnRNAP A2/B1 (1:1000; Sigma); Pan-hnRNP A/B (1:400 Mab clone 62); T7 tag (1:5,000; Novagen). Secondary antibodies: HRP-conjugated goat anti-mouse (1:10,000; Jackson Laboratories).

Growth Curves:

U87MG or NIH 3T3 cells were infected with the indicated retroviruses. After selection, 5,000 cells per well were seeded in 96-well plates. Cells were fixed and stained with methylene blue as described (Karni et al., Nat Struct Mol Biol 2007; 14: 185-93), and the A650 of the acid-extracted stain was measured on a plate reader (BioRad).

RT-PCR:

Total RNA was extracted with Trizol reagent (Sigma) and 2 μg of total RNA was reverse transcribed with AffinityScript II (Stratagene) RT. PCR was performed on 1/10 (1-2 μl) of the cDNA, in 25-50-1 μl reactions containing 0.2 mM dNTP mix, 10×PCR buffer with 15 mM $MgCl_2$ (Invitrogen), 2.5 units of TaqGold (Invitrogen) and 0.2 μM of each primer; 5% (v/v) DMSO was included in some reactions. PCR conditions were 95° C. for 5 min, then 35 cycles of 94° C. for 30 s, 57° C. for 30 s and 72° C. for 45 s, followed by 10 min at 72° C. PCR products were separated on 1.5% or 2% agarose gels or on 6% non-denaturing polyacrylamide gels.

Primers are described in Table 1, herein below.

TABLE 1

| | |
|---|---|
| HNRNP A1 | For-GTGGCTTTGGTGGCAGCCGTG (SEQ ID NO: 1)<br>Rev-CATTGTAGCTTCCACCACCTCC (SEQ ID NO: 2) |
| MST1R (RON) | For-TGTGAGAGGCAGCTTCCAGCAG (SEQ ID NO: 3)<br>Rev-CTAGCTGCTTCCTCCGCCAC (SEQ ID NO: 4) |
| ENAH-11 (MENA11) | For-GAGAAGAATTGCTGAAAAG (SEQ ID NO: 5)<br>Rev-TGGGCTGTGATAAGGGTGT (SEQ ID NO: 6) |
| WWOX | E5 For-CACTGGCAAAGTGGTTGTGGTC (SEQ ID NO: 7)<br>E9 Rev-GGTGGTGGCAGCTCCCTGTTG (SEQ ID NO: 8) |
| CFLAR-long (FLIP1) | For-CTTGGCCAATTTGCCTGTAT (SEQ ID NO: 9)<br>Rev-GGCAGAAACTCTGCTGTTCC (SEQ ID NO: 10) |
| CFLAR-short (FLIPs) | For-CGAGGCAAGATAAGCAAGGA (SEQ ID NO: 11)<br>Rev-CACATGGAACAATTTCCAAGAA (SEQ ID NO: 12) |
| BIN1 | E11 For-CCTCCAGATGGCTCCCCTGC (SEQ ID NO: 13)<br>E14 Rev-CCCGGGGGCAGGTCCAAGCG (SEQ ID NO: 14) |
| GAPDH | For-ATCAAGAAGGTGGTGAAGCAG (SEQ ID NO: 15)<br>Rev-CTTACTCCTTGGAGGCCATGT (SEQ ID NO: 16) |
| SMN1/2 | For-CCCCCACCACCTCCCATATGTCC (SEQ ID NO: 17)<br>Rev-TATCTTCTATAACGCTTCACATTC (SEQ ID NO: 18) |
| CASP9 | E2 For-AGACCAGTGGACATTGGTTC (SEQ ID NO: 19)<br>E7 Rev-GGTCCCTCCAGGAAACAAA (SEQ ID NO: 20) |
| CASP8 | For-GGGATACTGTCTGATCATCAAC (SEQ ID NO: 21)<br>Rev-GGAGAGGATACAGCAGATGAA (SEQ ID NO: 22) |
| CASP2 | For-TTACCTGCACACCGAGTCAC (SEQ ID NO: 23)<br>Rev-TGGTTCTTTCCATCTTGTTGGTC (SEQ ID NO: 24) |
| DLK1 | For-CGCCAGGAGCCGGACCCGCGC (SEQ ID NO: 25)<br>Rev-GCCAGGGGGGCACAGGCAG (SEQ ID NO: 26) |
| CTNND1 | For-TGCCCTGCTGGATTTGTCTT (SEQ ID NO: 27)<br>Rev-TGCTGCAGCTGGCTCAAGTCA (SEQ ID NO: 28) |
| FGF4 | For-TTCTTCGTGGCCATGAGCAG (SEQ ID NO: 29)<br>Rev-CCGAAGAAAGTGCACCAAGG (SEQ ID NO: 30) |
| MKNK2 | For-CCAAGTCCTGCAGCACCCCTG (SEQ ID NO: 31)<br>Rev 13a-GATGGGAGGGTCAGGCGTGGTC (SEQ ID NO: 32)<br>Rev 13b-GAGGAGGAAGTGACTGTCCCAC (SEQ ID NO: 33) |
| CD 44 | For-AGGAGCAGCACTTCAGGAGGTTAC (SEQ ID NO: 34)<br>Rev-ACTGGGGTGGAATGTGTCTTGGTC (SEQ ID NO: 35) |

TABLE 1-continued

| | |
|---|---|
| CASP4 | For-GCTCTTCAACGCCACACAACGTG (SEQ ID NO: 36)<br>Rev e8-GGAAAGAGGTAGAAATATCTTGTC (SEQ ID NO: 37)<br>Rev e9-TTATTGAAATACAAAATGTTAAATATGC (SEQ ID NO: 38) |
| CARD9 | For-GGCGCCGCGCTCATGCGGAACC (SEQ ID NO: 39)<br>Rev-GATGGCCTCGATGCGGTCCTTG (SEQ ID NO: 40) |
| B-MYB | For-CCACACATGCAGCTACCCCG (SEQ ID NO: 41)<br>Rev-CACAGTCTGGTCTCTATGAAATGG (SEQ ID NO: 42) |
| Bcl-x | For-ATGTCTCAGAGCAACCGGGA (SEQ ID NO: 43)<br>Rev-TCACTTCCGACTGAAGAGTG (SEQ ID NO: 44) |
| SRSF6 | For-TACGGCTTCGTGGAGTTCGAGG (SEQ ID NO: 45)<br>Rev e4- CTGGATCTGCTTCCAGAGTAAGA (SEQ ID NO: 46)<br>Rev e3B- GGCAAAAGGCTGCTGTCGTCATGG (SEQ ID NO: 47) |
| RPS6KB1 | For e5: CTCTACCTCATCCTTGAGTATCTCAGTG (SEQ ID NO: 48)<br>Rev e6c: CTCAAAAGAATAAAGGGCTGAATC (SEQ ID NO: 49<br>Rev e7: CTTGGTGATTAAGCATGAT (SEQ ID NO: 50) |

hnRNP A2/B1 shRNA:
HNRNP A2/B1- sh1: CTGTTTGTTGGCGGAATTA (SEQ ID NO: 51)
sh2: CCATGGGCTTCACTGTATA (SEQ ID NO: 52)
hnRNP A2/B1 primers for Q-RT-PCR:
For: TTTGATGACCATGATCCTGT (SEQ ID NO: 53)
Rev: CTCTGAACTTCCTGCATTTC (SEQ ID NO: 54)

Results

The Splicing Factor hnRNP A2/B1 is Upregulated in Brain Cancers.

The expression of hnRNP A2/B1 in several types of brain cancers was analyzed using the Oncomine database (www.oncomine.org) and it was found that hnRNP A2/B1 is overexpressed in tumor samples from glioblastoma, oligodendroglioma and astrocytoma patients compared to normal brain tissues (FIG. 3A). The present inventors further analyzed 3 normal brain (blue bars) and 22 glioblastoma grade IV tumor samples by Q-RT-PCR and found that in 19 out of the 22 tumors (red bars) hnRNP A2/B1 was overexpressed over two fold than the average expression in the normal brain samples (FIG. 3B).

The Expression and Gene Copy Number of the Splicing Factor hnRNP A2/B1 are Inversely Correlated with Glioma Patient Survival.

To determine if the splicing factor hnRNP A2/B1 plays a role in glioma development and patient survival, the present inventors correlated gene expression and copy number of hnRNP A2/B1 in patient tumors with their survival using the NCI REMBRANDT database (wwwdotcaintegratordotnci-dotnihdotgov/rembrandt/menudotdodot). A very significant inverse correlation P=2.62E-5) was found between patient survival and elevated expression or gene copy number of hnRNP A2/B1 (FIGS. 3C-D). These results indicate that patients with tumors harboring elevated copy number of hnRNPA2/B1 have poor prognosis of survival. Analysis of the same samples for overexpression of known oncogenes (MYC and EGFR) or down-regulation of know tumor suppressors (TP53 and TP73) did not show significant correlation with patients survival (FIGS. 4A-D and 5A-D). Gene copy number of the tumor suppressor PTEN however, showed significant correlation with patient survival and AKT2 expression and copy numbers were also inversely-correlated with patient survival (FIGS. 6A-D). It is important to mention that hnRNP A2/B1 prognostic value was statistically better than AKT2 (FIGS. 3C-D) and thus it might be a better bio-marker for glioma prognosis. Interestingly, none of the other splicing factors from the hnRNP A/B protein family (hnRNP A1, hnRNP A0, hnRNP A3) or SR protein family showed significant inverse correlation with patient survival (FIGS. 7A-C).

hnRNP A2/B1 is Required for Glioblastoma Tumorigenicity and it can Transform NIH 3T3 Cells.

To examine the importance of hnRNP A2/B1 to glioma tumor maintenance, hnRNP A2/B1 was knocked-down in U87MG and T98G or over-expressed in the U87MG glioblastoma cell lines, and anchorage-independent growth was analyzed by colony formation in soft agar. Colony formation of U87MG and T98G cells with hnRNP A2/B1 knockdown was reduced in contrast to increased colony number and size in glioblastoma cells overexpress sing hnRNP A2/B1 FIGS. 8A-C, E-G; FIGS. 9A-C).

One of the features that can contribute to colony formation is the proliferation rate of the cells. Notably, for tumor development and progression other aspects such as motility, invasiveness, the ability to grow in an anchorage-independent manner and to resist apoptotic cues can be more prominent. To examine if hnRNP A2/B1 plays a role in proliferation, proliferation rates of U87MG glioblastoma cells were measured with up and down-regulation of hnRNP A2/B1. hnRNP A2/B1 knockdown did not reduce the viability of the glioblastoma cells and slightly inhibited their ability to proliferate on plastic in 10% serum but inhibited their proliferation in lower serum concentrations (FIG. 8D, FIG. 10) suggesting that hnRNP A2/B1 contributes to cell proliferation in low growth factor conditions. Importantly, in hnRNP A2/B1 knockdown and overexpression cell pools hnRNP A2/B1 silencing and overexpression was sustained over the growth curve period eliminating the possibility that cell density or an aberrant clone could overcome hnRNP A2/B1 silencing (FIGS. 10G-H) However, overexpression of hnRNP A2/B1 increased the proliferation rate of U87MG and NIH 3T3 cells in all growth factor concentrations (FIGS. 8H, 11D, 10A-C) indicating that it can contribute to enhance proliferation at both low and high growth factor conditions when overexpressed. In order to determine the importance of hnRNP A2/B1 for glioma tumor formation in vivo, nude mice were injected with U87MG cells with and without knockdown of hnRNP A2/B1. Cells with empty vector gave rise to fast growing large tumors while mice injected with U87MG cells where hnRNP A2/B1 was knocked-down developed either small tumors in some of the injection sites or no tumors at all (FIGS. 8I, J). The importance of hnRNP A2/B1 to brain cancer maintenance was also confirmed in the T98G glioma cell line (FIGS. 9A-C). T98G cells with hnRNP A2/B1 knockdown showed reduced colony formation in soft agar, similar to results in U87MG cells (FIGS. 9A-C).

hnRNP A2/B1 Overexpression Transformed NIH 3T3 and Converted them to be Tumorigenic.

Based on the results that hnRNP A2/B1 is required for the glioblastoma transformed phenotype, the present inventors examined the ability of this factor to transform normal immortal cells. Up regulation of hnRNP A2/B1 in NIH 3T3 cells induced colony formation in soft agar in contrast to control cells that did not form colonies (FIGS. 11A-C). Moreover, these cells formed fast-growing tumors when injected subcutaneously into nude mice (FIGS. 11E, F). Pathological analysis of the tumors formed by cells overexpressing hnRNPA2/B1 showed that these tumors look like high-grade invasive sarcoma with high mitotic index (FIG. 11G). These results suggest that hnRNP A2/B1 is a driving oncogene on its own and probably directly contributes to glioblastoma development.

hnRNP A2/B1 Levels Affects the Alternative Splicing of Several Tumor Suppressors and Oncogenes.

To examine the effect of hnRNP A2/B1 on alternative splicing in glioma tumor cells, the present inventors analyzed the alternative splicing pattern of several genes for which alternatively spliced isoforms have been characterized and for some of them shown to contribute to transformation invasion and apoptosis or to be affected by hnRNP A2/B1 (FIG. 12, FIGS. 13A-B). Alternative splicing changes induced by overexpression or knockdown of hnRNP A2/B1 are presented in Table 2, herein below.

TABLE 2

| Gene | Isoforms | hnRNP A2/B1 knockdown | hnRNP A2/B1 overexpression |
|---|---|---|---|
| HNRNP A1 (exon7B) | 2 | Inclusion | Skipping |
| SMN ½ (exon 7) | 2 | Inclusion | ND |
| CASP 2 (exon 9) | 2 | Inclusion | ND |
| CASP 8 (exon 8a) | 2 | NE | Inclusion |
| DLK1 (exon 5) | 2 | Inclusion | ND |
| CTNND1 (exon 2, 3) | 4 | Inclusion | NE |
| MKNK2 (Last exon) | 2 | exon 13 A | exon13 B |
| FGF4 (exon 2) | 2 | Inclusion | ND |
| SRSF 6 (exon 3B) | 2 | Inclusion | ND |
| RPS6KB1 (exon 6C) | 2 | NE | ND |

NE: No effect;
ND: Not determined

For the following additional genes, only a single isoform was detected: CASP4, BMYB, CD44 and CARD 9.

For Bcl-x, the long isoform is down-regulated by knockdown of hnRNP A2/B1.

Figures 12A, 12B, 12C, 12D, 12E:
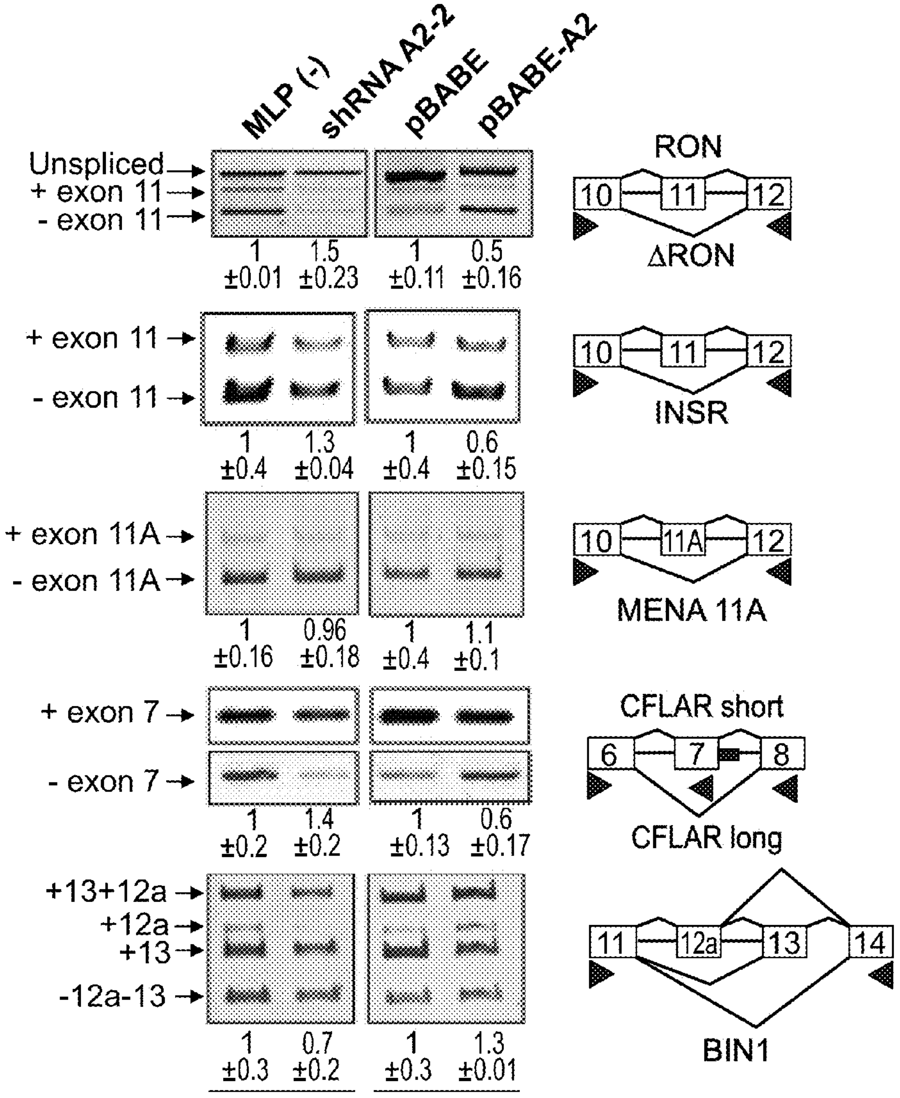
Figures 12F, 12G, 12H:
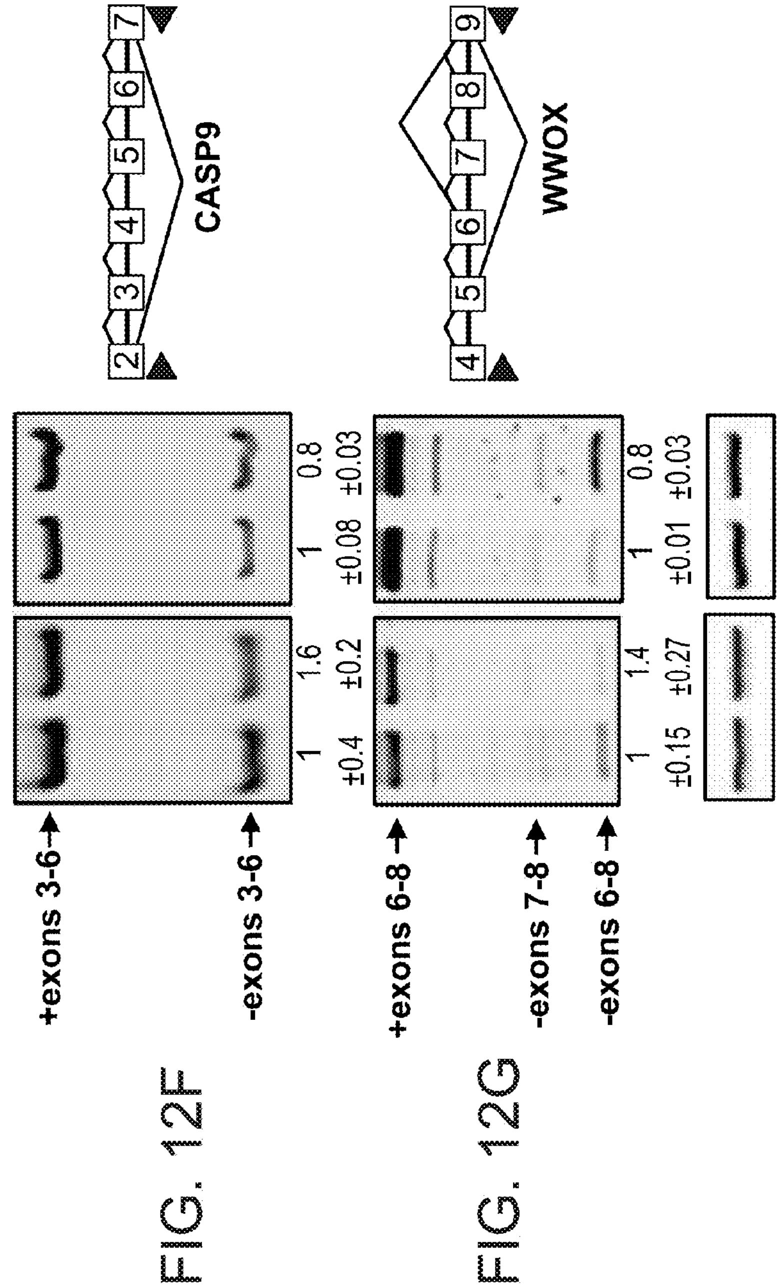

Knock-down of hnRNP A2/B1 in U87MG cells increased the inclusion while up-regulation of hnRNP A2/B1 increased the skipping of exon 11 of RON, a tyrosine kinase receptor involved in the invasiveness and motility of tumor cells (FIG. 12A). These results suggest that similar to the splicing factor oncoprotein SRSF1 (SF2/ASF), hnRNP A2/B1 up-regulation contributes to cellular transformation by increased skipping and up-regulation of the ΔRON oncogenic splicing isoform (Ghigna et al., Mol Cell 2005; 20: 881-90). Importantly, the levels of SRSF1 (SF2/ASF) or SRSF6 (SRp55), another SR protein and the levels of hnRNP A1, another hnRNP A/B family member did not change upon hnRNP A2/B1 down- or up-regulation (FIG. 14). In NIH 3T3 cells overexpressing hnRNP A2 we could only detect one isoform of RON suggesting that either this splicing event occurs only in humans or that it is hardly occurs in fibroblasts. The insulin receptor (IR) is the main mediator of insulin metabolism and glucose levels in the body and is expressed in most tissues. Skipping of exon 11 from the INSR transcript generates the splicing variant IR-A which binds the growth factor IGF-II in addition to insulin, is overproduced in many cancers and has been implicated in an autocrine loop in cancer cells hnRNP A2/B1 knockdown increased the inclusion of exon 11 while its overexpression increased exon 11 skipping generating the mitogenic isoform (FIG. 12B). The ENAH gene has been shown to play a role the in epithelial to mesenchymal transition (EMT) process and to affect cellular motility and invasion. Overexpression did not affect the inclusion of exon 11a suggesting that it is not a splicing target of hnRNP A2/B1 in U87MG cells (FIG. 12C). CFLAR (c-FLIP) is an anti-apoptotic protein that is alternatively spliced, and have been shown to inhibit TNF and TRAIL-induced apoptosis, but also to enhance motility and invasion through activation of the MAPK-ERK pathway. It was found that hnRNP A2/B1 down-regulation decreased the levels of the long isoform of c-FLIP while overexpression of hnRNP A2/B1 increased the level of the long isoform raising the possibility that upon hnRNP A2/B1 knockdown glioma cells might become more sensitive to apoptotic stimuli and in the same time be less motile and less invasive (31) (FIG. 12D). The tumor suppressor BIN1 has been shown to be regulated by alternative splicing and inclusion of exon 12a of BIN1 inactivates its tumor suppressor activity. BIN1 exon 12a was also identified as a target of the SR protein SRSF1 (SF2/ASF). The present inventors found that similar to the effect of SRSF1 overexpression, hnRNP A2/B1 overexpression in both U87MG and in NIH 3T3 enhanced exon 12a inclusion generating the anti-apoptotic isoform of BIN1 while its knockdown enhanced exon 12a skipping (FIG. 12E and FIG. 13). CASP9, the gene coding for Caspase-9 has been previously shown to be alternatively spliced by skipping of exons 3-6 and to generate a truncated dominant negative isoform that inhibits apoptosis and it overexpressed in several cancers. The present inventors found that hnRNP A2/B1 knockdown enhanced the production of full-length caspase-9 while its overexpression enhanced skipping of exons 3-6 generating the anti-apoptotic isoform Caspase 9B (FIG. 12F). WWOX is a known tumor suppressor which resides in common fragile site and is frequently inactivated in several types of cancer including glioblastoma. Skipping of exons 6-8 of WWOX have been reported in breast cancer. The present inventors found that hnRNP A2/B1 knockdown enhanced inclusion of alternatively spliced exons 6-8 while its overexpression induced skipping of these exons (FIG. 12G). Skipping of these exons causes deletion of 180 amino acids including its substrate binding domain and its alcohol dehydrogenase (ADH) domain probably inactivating its catalytic activity. However, the functional role of these skipped isoforms requires further examination. Wwox tumor suppressive activity is related to its anti-invasive and anti-apoptotic functions which are a common theme shared with the other targets of hnRNP A2/B1 we identified. hnRNP A2/B1 also affected the alternative splicing of exon 7B of hnRNP A1, another member of the hnRNP splicing factor family (FIGS. 13 and 14A). The levels of hnRNP A2/B1 also affected the alternative splicing of other genes, including known hnRNP A2/B1 targets such as exon 7 of the SMN gene and other splicing events (FIG. 13, Table 2). Importantly, many splicing events that were examined were not affected by hnRNP A2/B1 depletion or overexpression.

Knockdown of RON Reverses Transformation of Glioblastoma Cells Overexpressing hnRNP A2/B1.

In order to examine if RON contributes to hnRNP A2/B1-mediated transformation, the expression of the RON proto-oncogene was knocked down in U87MG cells overexpressing ectopic hnRNP A2. (FIG. 15A). It was found that stable knockdown by two different shRNA reduced RON levels and inhibited colony formation in soft agar of U87MG cells (FIGS. 15B-C). These results indicated that RON is one of the important mediators of hnRNP A2/B1 oncogenic activity in glioblastoma cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating breast cancer that has metastasized to a lung of a subject in need thereof, the method comprising administering to the subject a therapeutically effective amount of a polynucleotide agent which down-regulates an amount of hnRNP A2/B1 or a target thereof, thereby treating the breast cancer.

2. The method of claim 1, wherein said polynucleotide agent is an antisense polynucleotide.

3. The method of claim 1, wherein said polynucleotide agent is an siRNA.

4. The method of claim 1, wherein said target is hnRNP A1.

* * * * *

UNITED STATES PATENT AND TRADEMARK OFFICE

CERTIFICATE OF CORRECTION

PATENT NO. : 9,187,787 B2
APPLICATION NO. : 13/704701
DATED : November 17, 2015
INVENTOR(S) : Rotem Karni It is certified that error appears in the above-identified patent and that said Letters Patent is hereby corrected as shown below:

Title page,

Item [60] Related U.S. Application Data, insert the following:

--Provisional application No. 61/355,170, filed on June 16, 2010--

Signed and Sealed this
Twenty-sixth Day of April, 2016

Michelle K. Lee

Michelle K. Lee
*Director of the United States Patent and Trademark Office*

SEQUENCE LISTING

<160> NUMBER OF SEQ ID NOS: 59

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
gtggctttgg tggcagccgt g 21

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
cattgtagct tccaccacct cc 22

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
tgtgagaggc agcttccagc ag 22

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
ctagctgctt cctccgccac 20

<210> SEQ ID NO 5
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 5
gagaagaatt gctgaaaag 19

<210> SEQ ID NO 6
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 6
tgggctgtga taagggtgt 19

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
cactggcaaa gtggttgtgg tc 22

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
ggtggtggca gctccctgtt g 21

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
cttggccaat ttgcctgtat 20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
ggcagaaact ctgctgttcc 20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
cgaggcaaga taagcaagga 20

<210> SEQ ID NO 12
<211> LENGTH: 22
<212> TYPE: DNA
<213> ORGANISM: Artificial sequence
<220> FEATURE:

-continued

<223> OTHER INFORMATION: Single strand DNA oligonucleotide

<400> SEQUENCE: 12
cacatggaac aatttccaag aa 22

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
cctccagatg gctcccctgc 20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
cccgggggca ggtccaagcg 20

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15
atcaagaagg tggtgaagca g 21

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
cttactcctt ggaggccatg t 21

<210> SEQ ID NO 17
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 17
cccccaccac ctcccatatg tcc 23

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 18
tatcttctat aacgcttcac attc 24

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
agaccagtgg acattggttc 20

<210> SEQ ID NO 20
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 20
ggtccctcca ggaaacaaa 19

<210> SEQ ID NO 21
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 21
gggatactgt ctgatcatca ac 22

<210> SEQ ID NO 22
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 22
ggagaggata cagcagatga a 21

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
ttacctgcac accgagtcac 20

<210> SEQ ID NO 24
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 24
tggttctttc catcttgttg gtc 23

<210> SEQ ID NO 25
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 25
cgccaggagc cggacccgcg c 21

<210> SEQ ID NO 26
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 26
gccagggggg cacaggcag 19

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
tgccctgctg gatttgtctt 20

<210> SEQ ID NO 28
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 28
tgctgcagct ggctcaagtc a 21

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
ttcttcgtgg ccatgagcag 20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
ccgaagaaag tgcaccaagg 20

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 31
ccaagtcctg cagcacccct g 21

<210> SEQ ID NO 32
<211> LENGTH: 22

<212> TYPE: DNA
<213> ORGANISM: Artificial sequence
<220> FEATURE:
<223> OTHER INFORMATION: Single strand DNA oligonucleotide

<400> SEQUENCE: 32
gatgggaggg tcaggcgtgg tc 22

<210> SEQ ID NO 33
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 33
gaggaggaag tgactgtccc ac 22

<210> SEQ ID NO 34
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 34
aggagcagca cttcaggagg ttac 24

<210> SEQ ID NO 35
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 35
actggggtgg aatgtgtctt ggtc 24

<210> SEQ ID NO 36
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 36
gctcttcaac gccacacaac gtg 23

<210> SEQ ID NO 37
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 37
ggaaagaggt agaaatatct tgtc 24

<210> SEQ ID NO 38
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 38
ttattgaaat acaaaatgtt aaatatgc 28

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
ggcgccgcgc tcatgcggaa cc 22

<210> SEQ ID NO 40
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 40
gatggcctcg atgcggtcct tg 22

<210> SEQ ID NO 41
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 41
ccacacatgc agctaccccg 20

<210> SEQ ID NO 42
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 42
cacagtctgg tctctatgaa atgg 24

<210> SEQ ID NO 43
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 43
atgtctcaga gcaaccggga 20

<210> SEQ ID NO 44
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 44
tcacttccga ctgaagagtg 20

<210> SEQ ID NO 45
<211> LENGTH: 22
<212> TYPE: DNA
<213> ORGANISM: Artificial sequence -continued
<220> FEATURE:
<223> OTHER INFORMATION: Single strand DNA oligonucleotide

<400> SEQUENCE: 45
tacggcttcg tggagttcga gg 22

<210> SEQ ID NO 46
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 46
ctggatctgc ttccagagta aga 23

<210> SEQ ID NO 47
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 47
ggcaaaaggc tgctgtcgtc atgg 24

<210> SEQ ID NO 48
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 48
ctctacctca tccttgagta tctcagtg 28

<210> SEQ ID NO 49
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 49
ctcaaaagaa taaagggctg aatc 24

<210> SEQ ID NO 50
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 50
cttggtgatt aagcatgat 19

<210> SEQ ID NO 51
<211> LENGTH: 19
<212> TYPE: DNA
<213> ORGANISM: Artificial sequence
<220> FEATURE:
<223> OTHER INFORMATION: hnRNP A2/B1 shRNA target sequence

<400> SEQUENCE: 51
ctgtttgttg gcggaatta 19

<210> SEQ ID NO 52
<211> LENGTH: 19
<212> TYPE: DNA
<213> ORGANISM: Artificial sequence
<220> FEATURE:
<223> OTHER INFORMATION: hnRNP A2/B1 shRNA target sequence

<400> SEQUENCE: 52
ccatgggctt cactgtata 19

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 53
tttgatgacc atgatcctgt 20

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
ctctgaactt cctgcatttc 20

<210> SEQ ID NO 55
<211> LENGTH: 3666
<212> TYPE: DNA
<213> ORGANISM: Homo sapiens

<400> SEQUENCE: 55
agtggggggg aaggttctag aaaagcggcg gcagcggctc tagcggcagt agcagcagcg 60
ccgggtcccg tgcggaggtg ctcctcgcag agttgtttct cgagcagcgg cagttctcac 120
tacagcgcca ggacgagtcc ggttcgtgtt cgtccgcgga gatctctctc atctcgctcg 180
gctgcgggaa atcgggctga agcgactgag tccgcgatgg agagagaaaa ggaacagttc 240
cgtaagctct ttattggtgg cttaagcttt gaaaccacag aagaaagttt gaggaactac 300
tacgaacaat ggggaaagct tacagactgt gtggtaatga gggatcctgc aagcaaaaga 360
tcaagaggat ttggttttgt aactttttca tccatggctg aggttgatgc tgccatggct 420
gcaagacctc attcaattga tgggagagta gttgagccaa aacgtgctgt agcaagagag 480
gaatctggaa aaccaggggc tcatgtaact gtgaagaagc tgtttgttgg cggaattaaa 540
gaagatactg aggaacatca ccttagagat tactttgagg aatatggaaa aattgatacc 600
attgagataa ttactgatag gcagtctgga aagaaaagag gctttggctt tgttactttt 660
gatgaccatg atcctgtgga taaaatcgta ttgcagaaat accataccat caatggtcat 720
aatgcagaag taagaaaggc tttgtctaga caagaaatgc aggaagttca gagttctagg 780
agtggaagag gaggcaactt tggctttggg gattcacgtg gtggcggtgg aaatttcgga 840
ccaggaccag gaagtaactt tagaggagga tctgatggat atggcagtgg acgtggattt 900
ggggatggct ataatgggta tggaggagga cctggaggtg gcaattttgg aggtagcccc 960
ggttatggag gaggaagagg aggatatggt ggtggaggac ctggatatgg caaccagggt 1020
gggggctacg gaggtggtta tgacaactat ggaggaggaa attatggaag tggaaattac 1080

```
aatgattttg gaaattataa ccagcaacct tctaactacg gtccaatgaa gagtggaaac   1140
tttggtggta gcaggaacat ggggggacca tatggtggag gaaactatgg tccaggaggc   1200
agtggaggaa gtgggggtta tggtgggagg agccgatact gagcttcttc ctatttgcca   1260
tgggcttcac tgtataaata ggagaggatg agagcccaga ggtaacagaa cagcttcagg   1320
ttatcgaaat aacaatgtta aggaaactct tatctcagtc atgcataaat atgcagtgat   1380
atggcagaag acaccagagc agatgcagag agccattttg tgaatggatt ggattattta   1440
ataacattac cttactgtgg aggaaggatt gtaaaaaaaa atgcctttga gacagtttct   1500
tagcttttta attgttgttt ctttctagtg gtctttgtaa gagtgtagaa gcattccttc   1560
tttgataatg ttaaatttgt aagtttcagg tgacatgtga aacctttttt aagatttttc   1620
tcaaagtttt gaaaagctat tagccaggat catggtgtaa taagacataa cgtttttcct   1680
ttaaaaaaat ttaagtgcgt gtgtagagtt aagaagctgt tgtacattta tgatttaata   1740
aaataattct aaaggaaatt gtgtaattat agacttttta ttttaaataa gttaaggagt   1800
gggtagtata attaaggtcc gttgcaaagc tgttgttata tttgtataag ataaatgctg   1860
gtcagatgta agtgtgttgt ctgcaattca tcaggattaa attatgtaga taacttaagg   1920
gatatctctg caaggagaaa caccttttta gatcttttag atgctgcttc ttcaatgcaa   1980
ggaaaggaaa taaccccagc gaggtactct tcagggacac aggtctagta caagagaact   2040
cttgacggct actaagttca gccagtctta aaaaactgtg ctgtttctac aaaactttaa   2100
ctacagtagt ttataaggat gccaacgaaa gctgagggtg tagagcaaaa tagttctaag   2160
cttcagttaa acttctttag gtaagatctt atttactttt cctttcttaa ttttcctccc   2220
taaaagataa actaatactc ttaaatggtc tttcagtata gtggttctta cgtagtttaa   2280
catagctata aattgagttt aacaatttat aaactcaaga gaataatttt tataaaccct   2340
gttttccaat ctgtcattta cttaaattat tttggttgtt tttccctttt tttccttctt   2400
ttcccacccc ctccccctcc atgtgaagat ttgggtgctt aacatatcat ttttttccct   2460
gccggaattt tagcattgat atgaaccatg gacaagtata ttctgctgcc acaaagactg   2520
taaagtgctt catttcaaca gctgaggcaa gccaagtgat cattaataaa gcttttcttg   2580
gttccttcag tggtgttggt agtaaaatgg taggtaaaag ttaggctgca agttcaataa   2640
atcatgagat ttcccatcgt tacacccttg tgtattcaca tttcttggat caaacatttt   2700
gagtgaacta ggggttttta ttaaagacat ttgttgtatt tatggttgta actgtacatg   2760
cttatcagga tgagactgaa agaaggtagg gcaaaaatgg ttgaatctat tttcagatag   2820
tagttcatac ttgagtgaag tgtcttgtct gcattatgaa gcctggtatg tatccagtac   2880
taaataggtg ggttaaatgt ggtaattcta gttcagtgtc ttaccctgaa gagaaagttg   2940
taggttggct gttgaaattc attccttaga tatgatcagt ttgattgccc ggctttattg   3000
cctttacagg aatgtgatac tcagggctta ctctatacac caatgagtct tctttgatcc   3060
taagaccacc actgaagttg tttaggttct tttggacaaa catgataaac ttcttcagat   3120
acttttttt tcctttggca ggaaggtgtc ttgctgcagg taactaatga agaagtggtc   3180
aaccacagag tcttcaagaa ataagaaatt ctgtaccatc tgaaagtagt tcttgttggt   3240
gccttcattt aaaaagcact ctttaaaata aaagggaaat gttttctgat aaaacaaaca   3300
tttagttgag gttcttgata taaaacaatt acaaaatgag tgttgtttgt aaaacagtaa   3360
catcaaattg gctagagaga taaatgtatc atgttttaaa ttaggttttg tgagtagaca   3420
```

-continued gattacaatt ctattttaaa tataaagttt ataaaataaa tactttttgt atccaaatac 3480
ttggtgtaat gtttacacat aaaatgtgtg aatcttgttc tataaatatt tggttgtcta 3540
aaagatcacc atcccctaaa tttttaaaag cagtttcaca aagctatgca tattttaata 3600
ttaacaggta aatgagaaga gcattgtgga cattattggc tgtccccaat aaaatgctgt 3660
tcatta 3666

<210> SEQ ID NO 56
<211> LENGTH: 3702
<212> TYPE: DNA
<213> ORGANISM: Homo sapiens

<400> SEQUENCE: 56
agtggggggg aaggttctag aaaagcggcg gcagcggctc tagcggcagt agcagcagcg 60
ccgggtcccg tgcggaggtg ctcctcgcag agttgtttct cgagcagcgg cagttctcac 120
tacagcgcca ggacgagtcc ggttcgtgtt cgtccgcgga gatctctctc atctcgctcg 180
gctgcgggaa atcgggctga agcgactgag tccgcgatgg agaaaacttt agaaactgtt 240
cctttggaga ggaaaaagag agaaaaggaa cagttccgta agctctttat tggtggctta 300
agctttgaaa ccacagaaga aagtttgagg aactactacg aacaatgggg aaagcttaca 360
gactgtgtgg taatgaggga tcctgcaagc aaaagatcaa gaggatttgg ttttgtaact 420
ttttcatcca tggctgaggt tgatgctgcc atggctgcaa gacctcattc aattgatggg 480
agagtagttg agccaaaacg tgctgtagca agagaggaat ctggaaaacc aggggctcat 540
gtaactgtga agaagctgtt tgttggcgga attaaagaag atactgagga acatcacctt 600
agagattact ttgaggaata tggaaaaatt gataccattg agataattac tgataggcag 660
tctggaaaga aaagaggctt tggctttgtt acttttgatg accatgatcc tgtggataaa 720
atcgtattgc agaaatacca taccatcaat ggtcataatg cagaagtaag aaaggctttg 780
tctagacaag aaatgcagga agttcagagt tctaggagtg gaagaggagg caactttggc 840
tttggggatt cacgtggtgg cggtggaaat ttcggaccag gaccaggaag taactttaga 900
ggaggatctg atggatatgg cagtggacgt ggatttgggg atggctataa tgggtatgga 960
ggaggacctg gaggtggcaa ttttggaggt agccccggtt atggaggagg aagaggagga 1020
tatggtggtg gaggacctgg atatggcaac cagggtgggg gctacggagg tggttatgac 1080
aactatggag gaggaaatta tggaagtgga aattacaatg attttggaaa ttataaccag 1140
caaccttcta actacggtcc aatgaagagt ggaaactttg gtggtagcag gaacatgggg 1200
ggaccatatg gtggaggaaa ctatggtcca ggaggcagtg gaggaagtgg gggttatggt 1260
gggaggagcc gatactgagc ttcttcctat ttgccatggg cttcactgta taaataggag 1320
aggatgagag cccagaggta acagaacagc ttcaggttat cgaaataaca atgttaagga 1380
aactcttatc tcagtcatgc ataaatatgc agtgatatgg cagaagacac cagagcagat 1440
gcagagagcc attttgtgaa tggattggat tatttaataa cattacctta ctgtggagga 1500
aggattgtaa aaaaaaatgc ctttgagaca gtttcttagc tttttaattg ttgtttcttt 1560
ctagtggtct ttgtaagagt gtagaagcat tccttctttg ataatgttaa atttgtaagt 1620
ttcaggtgac atgtgaaacc tttttttaaga tttttctcaa agttttgaaa agctattagc 1680
caggatcatg gtgtaataag acataacgtt tttcctttaa aaaaatttaa gtgcgtgtgt 1740
agagttaaga agctgttgta catttatgat ttaataaaat aattctaaag gaaattgtgt 1800
aattatagac tttttatttt aaataagtta aggagtgggt agtataatta aggtccgttg 1860

```
caaagctgtt gttatatttg tataagataa atgctggtca gatgtaagtg tgttgtctgc   1920
aattcatcag gattaaatta tgtagataac ttaagggata tctctgcaag gagaaacacc   1980
tttttagatc ttttagatgc tgcttcttca atgcaaggaa aggaaataac cccagcgagg   2040
tactcttcag ggacacaggt ctagtacaag agaactcttg acggctacta agttcagcca   2100
gtcttaaaaa actgtgctgt ttctacaaaa ctttaactac agtagtttat aaggatgcca   2160
acgaaagctg agggtgtaga gcaaaatagt tctaagcttc agttaaactt ctttaggtaa   2220
gatcttattt acttttcctt tcttaatttt cctccctaaa agataaacta atactcttaa   2280
atggtctttc agtatagtgg ttcttacgta gtttaacata gctataaatt gagtttaaca   2340
atttataaac tcaagagaat aatttttata aaccctgttt tccaatctgt catttactta   2400
aattattttg gttgttttc cctttttttc cttcttttcc cacccctcc ccctccatgt   2460
gaagatttgg gtgcttaaca tatcattttt ttccctgccg gaattttagc attgatatga   2520
accatggaca agtatattct gctgccacaa agactgtaaa gtgcttcatt tcaacagctg   2580
aggcaagcca agtgatcatt aataaagctt ttcttggttc cttcagtggt gttggtagta   2640
aaatggtagg taaaagttag gctgcaagtt caataaatca tgagatttcc catcgttaca   2700
cccttgtgta ttcacatttc ttggatcaaa cattttgagt gaactagggg tttttattaa   2760
agacatttgt tgtatttatg gttgtaactg tacatgctta tcaggatgag actgaaagaa   2820
ggtagggcaa aaatggttga atctattttc agatagtagt tcatacttga gtgaagtgtc   2880
ttgtctgcat tatgaagcct ggtatgtatc cagtactaaa taggtgggtt aaatgtggta   2940
attctagttc agtgtcttac cctgaagaga aagttgtagg ttggctgttg aaattcattc   3000
cttagatatg atcagtttga ttgcccggct ttattgcctt tacaggaatg tgatactcag   3060
ggcttactct atacaccaat gagtcttctt tgatcctaag accaccactg aagttgttta   3120
ggttcttttg gacaaacatg ataaacttct tcagatactt tttttttcct ttggcaggaa   3180
ggtgtcttgc tgcaggtaac taatgaagaa gtggtcaacc acagagtctt caagaaataa   3240
gaaattctgt accatctgaa agtagttctt gttggtgcct tcatttaaaa agcactcttt   3300
aaaataaaag ggaaatgttt tctgataaaa caaacattta gttgaggttc ttgatataaa   3360
acaattacaa aatgagtgtt gtttgtaaaa cagtaacatc aaattggcta gagagataaa   3420
tgtatcatgt tttaaattag gttttgtgag tagacagatt acaattctat tttaaatata   3480
aagtttataa aataaatact ttttgtatcc aaatacttgg tgtaatgttt acacataaaa   3540
tgtgtgaatc ttgttctata aatatttggt tgtctaaaag atcaccatcc cctaaatttt   3600
taaaagcagt ttcacaaagc tatgcatatt ttaatattaa caggtaaatg agaagagcat   3660
tgtggacatt attggctgtc cccaataaaa tgctgttcat ta                      3702
```

<210> SEQ ID NO 57
<211> LENGTH: 1785
<212> TYPE: DNA
<213> ORGANISM: Homo sapiens

<400> SEQUENCE: 57

```
gagagggcga aggtaggctg gcagatacgt tcgtcagctt gctcctttct gcccgtggac     60
gccgccgaag aagcatcgtt aaagtctctc ttcaccctgc cgtcatgtct aagtcagagt    120
ctcctaaaga gcccgaacag ctgaggaagc tcttcattgg agggttgagc tttgaaacaa    180
ctgatgagag cctgaggagc cattttgagc aatggggaac gctcacggac tgtgtggtaa    240
```

-continued

```
tgagagatcc aaacaccaag cgctccaggg gctttgggtt tgtcacatat gccactgtgg    300
aggaggtgga tgcagctatg aatgcaaggc cacacaaggt ggatggaaga gttgtggaac    360
caaagagagc tgtctccaga gaagattctc aaagaccagg tgcccactta actgtgaaaa    420
agatatttgt tggtggcatt aaagaagaca ctgaagaaca tcacctaaga gattattttg    480
aacagtatgg aaaaattgaa gtgattgaaa tcatgactga ccgaggcagt ggcaagaaaa    540
ggggctttgc ctttgtaacc tttgacgacc atgactccgt ggataagatt gtcattcaga    600
aataccatac tgtgaatggc cacaactgtg aagttagaaa agccctgtca aagcaagaga    660
tggctagtgc ttcatccagc caaagaggtc gaagtggttc tggaaacttt ggtggtggtc    720
gtggaggtgg tttcggtggg aatgacaact tcggtcgtgg aggaaacttc agtggtcgtg    780
gtggctttgg tggcagccgt ggtggtggtg gatatggtgg cagtggggat ggctataatg    840
gatttggtaa tgatggaagc aattttggag gtggtggaag ctacaatgat tttgggaatt    900
acaacaatca gtcttcaaat tttggaccca tgaagggagg aaattttgga ggcagaagct    960
ctggccccta tggcggtgga ggccaatact ttgcaaaacc acgaaaccaa ggtggctatg   1020
gcggttccag cagcagcagt agctatggca gtggcagaag attttaatta ggaaacaaag   1080
cttagcagga gaggagagcc agagaagtga cagggaagct acaggttaca acagatttgt   1140
gaactcagcc aagcacagtg gtggcagggc ctagctgcta caaagaagac atgttttaga   1200
caaatactca tgtgtatggg caaaaaactc gaggactgta tttgtgacta attgtataac   1260
aggttatttt agtttctgtt ctgtggaaag tgtaaagcat tccaacaaag ggttttaatg   1320
tagatttttt tttttgcacc ccatgctgtt gattgctaaa tgtaacagtc tgatcgtgac   1380
gctgaataaa tgtctttttt ttaatgtgct gtgtaaagtt agtctactct taagccatct   1440
tggtaaattt ccccaacagt gtgaagttag aattccttca gggtgatgcc aggttctatt   1500
tggaatttat atacaacctg cttgggtgga gaagccattg tcttcggaaa ccttggtgta   1560
gttgaactga tagttactgt tgtgacctga agttcaccat taaaagggat tacccaagca   1620
aaatcatgga atggttataa aagtgattgt tggcacatcc tatgcaatat atctaaattg   1680
aataatggta ccagataaaa ttatagatgg gaatgaagct tgtgtatcca ttatcatgtg   1740
taatcaataa acgatttaat tctcttgaaa aaaaaaaaaa aaaaa                  1785
```

<210> SEQ ID NO 58
<211> LENGTH: 1941
<212> TYPE: DNA
<213> ORGANISM: Homo sapiens

<400> SEQUENCE: 58

```
gagagggcga aggtaggctg gcagatacgt tcgtcagctt gctcctttct gcccgtggac     60
gccgccgaag aagcatcgtt aaagtctctc ttcaccctgc cgtcatgtct aagtcagagt    120
ctcctaaaga gcccgaacag ctgaggaagc tcttcattgg agggttgagc tttgaaacaa    180
ctgatgagag cctgaggagc cattttgagc aatggggaac gctcacggac tgtgtggtaa    240
tgagagatcc aaacaccaag cgctccaggg gctttgggtt tgtcacatat gccactgtgg    300
aggaggtgga tgcagctatg aatgcaaggc cacacaaggt ggatggaaga gttgtggaac    360
caaagagagc tgtctccaga gaagattctc aaagaccagg tgcccactta actgtgaaaa    420
agatatttgt tggtggcatt aaagaagaca ctgaagaaca tcacctaaga gattattttg    480
aacagtatgg aaaaattgaa gtgattgaaa tcatgactga ccgaggcagt ggcaagaaaa    540
ggggctttgc ctttgtaacc tttgacgacc atgactccgt ggataagatt gtcattcaga    600
```

```
aataccatac tgtgaatggc cacaactgtg aagttagaaa agccctgtca aagcaagaga    660
tggctagtgc ttcatccagc caaagaggtc gaagtggttc tggaaacttt ggtggtggtc    720
gtggaggtgg tttcggtggg aatgacaact tcggtcgtgg aggaaacttc agtggtcgtg    780
gtggctttgg tggcagccgt ggtggtggtg gatatggtgg cagtggggat ggctataatg    840
gatttggtaa tgatggtggt tatggaggag gcggccctgg ttactctgga ggaagcagag    900
gctatggaag tggtggacag ggttatggaa accagggcag tggctatggc gggagtggca    960
gctatgacag ctataacaac ggaggcggag gcggctttgg cggtggtagt ggaagcaatt   1020
ttggaggtgg tggaagctac aatgattttg ggaattacaa caatcagtct tcaaattttg   1080
gacccatgaa gggaggaaat tttggaggca gaagctctgg cccctatggc ggtggaggcc   1140
aatactttgc aaaaccacga aaccaaggtg gctatggcgg ttccagcagc agcagtagct   1200
atggcagtgg cagaagattt taattaggaa acaaagctta gcaggagagg agagccagag   1260
aagtgacagg gaagctacag gttacaacag atttgtgaac tcagccaagc acagtggtgg   1320
cagggcctag ctgctacaaa gaagacatgt tttagacaaa tactcatgtg tatgggcaaa   1380
aaactcgagg actgtatttg tgactaattg tataacaggt tattttagtt tctgttctgt   1440
ggaaagtgta aagcattcca acaaagggtt ttaatgtaga tttttttttt tgcaccccat   1500
gctgttgatt gctaaatgta acagtctgat cgtgacgctg aataaatgtc tttttttttaa   1560
tgtgctgtgt aaagttagtc tactcttaag ccatcttggt aaatttcccc aacagtgtga   1620
agttagaatt ccttcagggt gatgccaggt tctatttgga atttatatac aacctgcttg   1680
ggtggagaag ccattgtctt cggaaacctt ggtgtagttg aactgatagt tactgttgtg   1740
acctgaagtt caccattaaa agggattacc caagcaaaat catggaatgg ttataaaagt   1800
gattgttggc acatcctatg caatatatct aaattgaata atggtaccag ataaaattat   1860
agatgggaat gaagcttgtg tatccattat catgtgtaat caataaacga tttaattctc   1920
ttgaaaaaaa aaaaaaaaaa a                                              1941
```

<210> SEQ ID NO 59
<211> LENGTH: 4785
<212> TYPE: DNA
<213> ORGANISM: Homo sapiens

<400> SEQUENCE: 59

```
agtgtacagc ggcggctggg gcggcaggtg aggcggctgg ggcgttgctg tcgtgcgtcc     60
gcaggcgtca ggtgctcaga cccgagggcc gggaagggat ttgggtttca caggaacctg    120
gggcgggggt ccgctatctt ggggctgtcg ggaccgctgc ttaaatttgg cccagtccag    180
acctcgagtc gggcccccag ccaggcccac gcccaggtcc aggcccaggc cggtagggat    240
cctctagggt cccagctcgc ctcgatggag ctcctcccgc cgctgcctca gtccttcctg    300
ttgctgctgc tgttgcctgc caagcccgcg gcgggcgagg actggcagtg cccgcgcacc    360
ccctacgcgg cctctcgcga ctttgacgtg aagtacgtgg tgcccagctt ctccgccgga    420
ggcctggtac aggccatggt gacctacgag ggcgacagaa atgagagtgc tgtgtttgta    480
gccatacgca atcgcctgca tgtgcttggg cctgacctga agtctgtcca gagcctggcc    540
acgggccctg ctggagaccc tggctgccag acgtgtgcag cctgtggccc aggaccccac    600
ggccctcccg gtgacacaga cacaaaggtg ctggtgctgg atcccgcgct gcctgcgctg    660
gtcagttgtg gctccagcct gcagggccgc tgcttcctgc atgacctaga gccccaaggg    720
```

-continued

```
acagccgtgc atctggcagc gccagcctgc ctcttctcag cccaccataa ccggcccgat    780
gactgccccg actgtgtggc cagcccattg ggcacccgtg taactgtggt tgagcaaggc    840
caggcctcct atttctacgt ggcatcctca ctggacgcag ccgtggctgc cagcttcagc    900
ccacgctcag tgtctatcag gcgtctcaag gctgacgcct cgggattcgc accgggcttt    960
gtggcgttgt cagtgctgcc caagcatctt gtctcctaca gtattgaata cgtgcacagc   1020
ttccacacgg gagccttcgt atacttcctg actgtacagc cggccagcgt gacagatgat   1080
cctagtgccc tgcacacacg cctggcacgg cttagcgcca ctgagccaga gttgggtgac   1140
tatcgggagc tggtcctcga ctgcagattt gctccaaaac gcaggcgccg gggggcccca   1200
gaaggcggac agccctaccc tgtgctgcgg gtggcccact ccgctccagt gggtgcccaa   1260
cttgccactg agctgagcat cgccgagggc caggaagtac tatttggggt ctttgtgact   1320
ggcaaggatg gtggtcctgg cgtgggcccc aactctgtcg tctgtgcctt ccccattgac   1380
ctgctggaca cactaattga tgagggtgtg gagcgctgtt gtgaatcccc agtccatcca   1440
ggcctccggc gaggcctcga cttcttccag tcgcccagtt tttgccccaa cccgcctggc   1500
ctggaagccc tcagccccaa caccagctgc cgccacttcc ctctgctggt cagtagcagc   1560
ttctcacgtg tggacctatt caatgggctg ttgggaccag tacaggtcac tgcattgtat   1620
gtgacacgcc ttgacaacgt cacagtggca cacatgggca caatggatgg gcgtatcctg   1680
caggtggagc tggtcaggtc actaaactac ttgctgtatg tgtccaactt ctcactgggt   1740
gacagtgggc agcccgtgca gcgggatgtc agtcgtcttg gggaccacct actctttgcc   1800
tctggggacc aggttttcca ggtacctatc caaggccctg gctgccgcca cttcctgacc   1860
tgtgggcgtt gcctaagggc atggcatttc atgggctgtg gctggtgtgg gaacatgtgc   1920
ggccagcaga aggagtgtcc tggctcctgg caacaggacc actgcccacc taagcttact   1980
gagttccacc cccacagtgg acctctaagg ggcagtacaa ggctgaccct gtgtggctcc   2040
aacttctacc ttcacccttc tggtctggtg cctgagggaa cccatcaggt cactgtgggc   2100
caaagtccct gccggccact gcccaaggac agctcaaaac tcagaccagt gccccggaaa   2160
gactttgtag aggagtttga gtgtgaactg gagcccttgg gcacccaggc agtggggcct   2220
accaacgtca gcctcaccgt gactaacatg ccaccgggca agcacttccg ggtagacggc   2280
acctccgtgc tgagaggctt ctctttcatg gagccagtgc tgatagcagt gcaacccctc   2340
tttggcccac gggcaggagg cacctgtctc actcttgaag gccagagtct gtctgtaggc   2400
accagccggg ctgtgctggt caatgggact gagtgtctgc tagcacgggt cagtgagggg   2460
cagcttttat gtgccacacc ccctggggcc acggtggcca gtgtccccct tagcctgcag   2520
gtggggggtg cccaggtacc tggttcctgg accttccagt acagagaaga ccctgtcgtg   2580
ctaagcatca gccccaactg tggctacatc aactcccaca tcaccatctg tggccagcat   2640
ctaacttcag catggcactt agtgctgtca ttccatgacg ggcttagggc agtggaaagc   2700
aggtgtgaga ggcagcttcc agagcagcag ctgtgccgcc ttcctgaata tgtggtccga   2760
gacccccagg gatgggtggc agggaatctg agtgcccgag gggatggagc tgctggcttt   2820
acactgcctg gctttcgctt cctaccccca ccccatccac ccagtgccaa cctagttcca   2880
ctgaagcctg aggagcatgc cattaagttt gagtatattg ggctgggcgc tgtggctgac   2940
tgtgtgggta tcaacgtgac cgtgggtggt gagagctgcc agcacgagtt ccggggggac   3000
atggttgtct gccccctgcc cccatccctg cagcttggcc aggatggtgc cccattgcag   3060
gtctgcgtag atggtgaatg tcatatcctg ggtagagtgg tgcggccagg gccagatggg   3120
```

-continued

```
gtcccacaga gcacgctcct tggtatcctg ctgcctttgc tgctgcttgt ggctgcactg   3180
gcgactgcac tggtcttcag ctactggtgg cggaggaagc agctagttct tcctcccaac   3240
ctgaatgacc tggcatccct ggaccagact gctggagcca cacccctgcc tattctgtac   3300
tcgggctctg actacagaag tggccttgca ctccctgcca ttgatggtct ggattccacc   3360
acttgtgtcc atggagcatc cttctccgat agtgaagatg aatcctgtgt gccactgctg   3420
cggaaagagt ccatccagct aagggacctg gactctgcgc tcttggctga ggtcaaggat   3480
gtgctgattc cccatgagcg ggtggtcacc cacagtgacc gagtcattgg caaaggccac   3540
tttggagttg tctaccacgg agaatacata gaccaggccc agaatcgaat ccaatgtgcc   3600
atcaagtcac taagtcgcat cacagagatg cagcaggtgg aggccttcct gcgagagggg   3660
ctgctcatgc gtggcctgaa ccacccgaat gtgctggctc tcattggtat catgttgcca   3720
cctgagggcc tgccccatgt gctgctgccc tatatgtgcc acggtgacct gctccagttc   3780
atccgctcac ctcagcggaa ccccaccgtg aaggacctca tcagctttgg cctgcaggta   3840
gcccgcggca tggagtacct ggcagagcag aagtttgtgc acagggacct ggctgcgcgg   3900
aactgcatgc tggacgagtc attcacagtc aaggtggctg actttggttt ggcccgcgac   3960
atcctggaca gggagtacta tagtgttcaa cagcatcgcc acgctcgcct acctgtgaag   4020
tggatggcgc tggagagcct gcagacctat agatttacca ccaagtctga tgtgtggtca   4080
tttggtgtgc tgctgtggga actgctgaca cggggtgccc caccataccg ccacattgac   4140
ccttttgacc ttacccactt cctggcccag ggtcggcgcc tgccccagcc tgagtattgc   4200
cctgattctc tgtaccaagt gatgcagcaa tgctgggagg cagacccagc agtgcgaccc   4260
accttcagag tactagtggg ggaggtggag cagatagtgt ctgcactgct tggggaccat   4320
tatgtgcagc tgccagcaac ctacatgaac ttgggcccca gcacctcgca tgagatgaat   4380
gtgcgtccag aacagccgca gttctcaccc atgccaggga atgtacgccg gccccggcca   4440
ctctcagagc ctcctcggcc cacttgactt agttcttggg ctggacctgc ttagctgcct   4500
tgagctaacc ccaagctgcc tctgggccat gccaggccag agggcagtgg ccctccacct   4560
tgttcctgcc ctttaacttt cagaggcaat aggtaaatgg ggcccattag gtccctcact   4620
ccacagagtg agccagtgag ggcagtcctg caacatgtat ttatggagtg cctgctgtgg   4680
accctgtctt ctgggcacag tggactcagc agtgaccaca ccaacactga cccttgaacc   4740
aataaaggaa caaatgacta ttaaagcaca aaaaaaaaaa aaaaa                   4785
```